US005663314A

United States Patent [19]

Seger et al.

[11] Patent Number: 5,663,314
[45] Date of Patent: Sep. 2, 1997

[54] HUMAN SIGNAL TRANSDUCTION MAPK KINASE

[75] Inventors: Rony Seger; Dalia Seger, both of Yavne, Israel; Natalie G. Ahn, Boulder, Colo.; Edwin G. Krebs, Seattle, Wash.

[73] Assignee: The Board of Regents of the University of Washington, Seattle, Wash.

[21] Appl. No.: 423,399

[22] Filed: Apr. 18, 1995

Related U.S. Application Data

[63] Continuation of Ser. No. 980,608, Nov. 20, 1992, abandoned.

[51] Int. Cl.$^6$ ................................................. C07H 21/04
[52] U.S. Cl. ................................................. 536/23.2
[58] Field of Search ................................................. 536/23.2

[56] References Cited

U.S. PATENT DOCUMENTS 5,405,941  4/1995  Johnson ................................. 530/350

OTHER PUBLICATIONS

Ray, L. B., and Sturgill, T. W. (1987) *Proc. Natl. Acad. Sci. U.S.A.* 84, 1502–1506.
Ray, L. B., and Sturgill, T. W. (1988) *J. Biol. Chem.* 263, 12721–12727.
Ahn, N. G., Weiel, J. E., Chan, C. P., and Krebs, E. G. (1990) *J. Biol. Chem.* 265, 11487 11494.
Anderson, N. G., Maller, J. L., Tonks, N. K., and Sturgill, T. W. (1990) *Nature* 343, 651–653.
Boulton, T. G., Yancopoulos, G. D., Gregory, J. S., Slaughter, C., Moomaw, C., Hsu, J., and Cobb, M. H. (1990) *Science* 249, 64–67.
Sturgill, T. W., and Wu, J. (1991) *Biochim. Bioshys. Acta* 1092, 350–357.
Cobb, M. H., Boulton, T. G., and Robbins, D. J. (1992) *Cell Regul.* 2, 965–978.
Thomas, G. (1992) *Cell* 68, 3–6.
Boulton, T. G., Gregory, J. S., and Cobb, M. H. (1991) *Biochemistry* 30, 278–286.
Boulton, T. G., Nye, S. H., Robbins, D. J., Y. N., Radziejewska, E., Morgenbesser, S., Depinho, R., Panayotatos, N., Cobb, M.H., and Yancopoulos, G. D. (1991) *Cell* 65, 663–675.
Pulverer, B. J., Kyriakis, J. M., Avruch, J., Nikolakaki, E., and Woodgett, J.R. (1991) *Nature* 253, 670–674.
Alvarez, E., Northwood, I. C., Gonzales, F. A., Latour, D. A., Seth, A., Abate, C., Curran, T., and Davis, R. J. (1991) *J. Biol. Chem.* 266,15277 15285.
Anderson, N. G., Li, P., Marsden, L. A., Williams, N., Roberts, T. M., and Sturgill, T. W. (1991) *Biochem. J.* 277, 573–576.
Takishima, K., Griswold–Prenner, I., Ingebritsen, T., and Rosner, M. R. (1991) *Proc. Natl. Acad. Sci. U.S.A.* 88 2520–2524.
Sturgill, T. W., Ray, L. B., Erickson, E., and Maller, J. L. (1988) *Nature* 334, 715–718.

Gregory, J. S., Boulton, T. G., Sang, B. C., and Cobb M. H. (1989) *J. Biol. Chem.* 264, 18397–18441.
Ahn, N. G., and Krebs, E. G. (1990) *J. Biol. Chem.* 265, 11495 11501.
Payne, D. M., Rossomando, A. J., Martino, P., Erickson, A. K., Her, J.–H., Shabanowitz, J., Hunt, D. F., Weber, M. J., and Sturgill, T. W. (1991) *EMBO J.* 10, 885 892.
Ahn, N. G., Seger, R., Bratlien, R. L., Diltz, C. D., Tonks N. K., and Krebs, E.G. (1991) *J. Biol. Chem.* 266, 4220–4227.
Gomez, N., and Cohen, P. (1991) *Nature* 353, 170–173.
Ahn, N. G., Robbins, D. J., Haycock, J. W., Seger, R., Cobb, M. H., and Krebs, E. G. (1992) *J. Neurochem.*, 59:147–156.
Seger, R., Ahn, N. G., Boulton, T. G., Yancopoulos, G. D., Panayotatos, N Radziejewska, E., Ericsson, L., Bratlein, R. L., Cobb, M. H., and Krebs, E. G. (1991) *Proc. Natl. Acad. Sci. U.S.A.* 88, 6142–6146.
Crews, C. M., Alessandrini, A. A., and Erikson, R. L. (1991) *Proc. Natl. Acad. Sci. U.S.A.* 88, 8845–8849.
Wu, T., Rossomando, A. J., Her, J.–H., Del–Vecchio, R., Weber, M. J., and Sturgill, T. W. (1991) *Proc. Natt. Acad. Sci. U.S.A.* 88, 9508–9512.
Robbins, D. J., and Cobb, M. H. (1992) *Mol. Biol. Cell* 3, 299–308.
Tonks, N. K., Charbonneau, H., Diltz, C. D., Fischer, E. H., and Walsh, K. A. (1988) *Biochemistry* 27, 8695 8701.
Cohen, P., Holmes, C. F. B., and Tsakitani, Y. (1990) *Trends Biochem. Sci.* 15, 98 102.
Posada, J., and Cooper, J. A. (1992) *Science* 255, 212–215.
Matsuda, S., Kosako, H., Takenaka, K., Moriyama, K., Sakai, H., Akiyama, T., Gotoh, Y., and Nishida, E. (1992) *EMBO J.* 11, 973–982.
Seger, R., Ahn, N.G., Posada, J., Munar, E.S. Jenson, A.M. Cooper, J.A., Cobb, M.H. and Krebs, E.G. (1992) *J. Biol. Chem.* 267, 14373–14381.
Kosako, Gotoh, Y., Matsuda, S., Ishikawa,M. and Nishida,E. (1992) *EMBOJ.* 11 , 2903–2908.
Shirakabe, K., Gotoh, Y. and Nishida, E. (1992) *J. Biol. Chem.* 267, 16685–16690.
Nakielny, S., Cohen, P., Wu, J. and Sturgill, T. (1992) *EMBO J.* 11, 2123–2128.
L'Allemain, G., Her, J.H., Wu, J., Sturgill, T.W. and Weber, M.J. (1992) *J. Mol. Cell Biol* 12, 2222–2229
Adams P.D. and Parker, P.J. (1 992) Activation of Mitogen–Activated Protein (MAP) Kinase by a MAP Kinase–Kinase *J. Biol. Chem.* 267, 13135–13138.
Rossomando, A., Wu, J., Weber, M.J. and Sturgill, T.W. (1992) *Proc. Natl. Acad. Sci. U.S.A.* 89, 5221–5225.
Hanks, S.K., Quinn, A.M. and Hunter T. (1988) *Science* 241, 42–52.

(List continued on next page.)

Primary Examiner—Vasu S. Jagannathan
Assistant Examiner—Brian Lathrop
Attorney, Agent, or Firm—Christensen O'Connor Johnson & Kindness PLLC

[57] ABSTRACT

An isolated nucleic acid molecule which hybridizes under stringent conditions with the nucleic acid shown in SEQ ID NO:32 or its complement or the nucleic acid shown in SEQ ID NO:34 or its complement, and which encodes mitogen activated protein kinase kinase protein.

4 Claims, No Drawings

OTHER PUBLICATIONS

Lee, M.G. and Nurse, P. (1987) *Nature* 327, 31–33.

Lindberg, R.A., Quinn, A.M. and Hunter, T. (1992) *Trends Biochem. Sci.* 17, 114–119.

Dent, P., Haser, W., Haystead, T.A.J., Vincent, L.A., Roberts, T.M. and Sturgill, T.W. (1992) *Science* 257, 1404–1406.

Higgins, D.G. and Sharp, P.M. (1988) *Gene* 73, 237–246.

Crews, C.M., Alessandrini, A., and Erikson, R.L. (1992; Oct.) *Science* 258, 478–480.

Crews, C.M., and Erikson, R.L. (1992: Sep.) *Proc. Natl. Acad. Sci. USA* 89, 8205–8209.

Nakielny, S., Campbell, D.G. and Cohen, P. (1992; Aug.) *FEBS* 308, 183–189.

Seger, R., Ahn, N.G., Bratlien, R.L., Cobb, M.H. and Krebs, E.G. (1991). Abstract, *15th Intl. Congress of Biochem.*, Jerusalem, Israel, Aug. 4–8, 1991.

Ahn, N.G., Seger, R.S., Bratlein, R.L., Tonks, N.K., and Krebs, E.G. (1990). Abstract, *Fed. Amer. Soc. Exptl. Biol. Med.*.

Suggs et al., PNAS, 78(1):6613–6617, 1981.

Young et al., PNAS, 80:1194–1198, 1983.

Seger et al. Human T–cell mitogen–activated protein kinase are related to yeast signal transduction kinases. The Journal of Biological Chemistry. vol. 267, No. 36, pp. 25628–25631. Dec. 25, 1992.

Adams et al. Sequence identification of 2,375 human brain genes. Nature. vol. 355, pp. 632–634. Feb. 13, 1992.

Crews et al. The primary structure of MEK, a protein kinase that phosphorylates the ERK gene product. Science. vol. 258, pp. 478–480. Oct. 16, 1992.

Molecular cloning: a laboratory manual, 2nd ed. Sambrook et al., eds. Cold Spring Harbor, Cold Spring Harbor Laboratory Press. Chapters 9 and 11 1989.

Teague et al. Nucleotide sequence of the yeast regulatory gene STE7 predicts a protein homologous to protein kinases. Proceedings of the National Academy of Sciences, USA. vol. 83, p. 7371–7375. Oct. 1988.

Ahn et al. Multiple components in an epidermal growth factor–stimulated protein kinase cascade: in vitro activation of a myelin basic protein/microtubule–associated protein 2 kinase. The Journal of Biological Chemistry. vol. 266, No. 7, pp. 4220–4227. Mar. 5, 1991.

Nadin–Davis et al. A gene which encodes a predicted protein kinase can restore functions of the ras gene in fission yeast. The EMBO Journal. vol. 7, No. 4, pp. 985–993. 1988.

Haystead et al. Ordered phosphorylation of p42mapk by MAP kinase kinase. FEBS Letters. vol. 306, No. 1, pp. 17–22. Jun. 1992.

HUMAN SIGNAL TRANSDUCTION MAPK KINASE

This is a continuation of application Ser. No. 07/980,608, filed Nov. 20, 1992, abandoned, the specification and drawings of which are incorporated by reference herein.

This invention was made with government support under grants DK42528 and GM42508 awarded by the National Institutes of Health. The government has certain rights in the invention.

FIELD OF THE INVENTION

The invention relates to molecular biology, isolated DNA, and protein for the human microtubule associated protein kinase kinase enzyme that is central in growth factor, hormone, cytokine, and neural-active signal transduction mechanisms.

BACKGROUND OF THE INVENTION

One of the early events in the response of cells to growth factors, hormones, immune cytokines, and neuropeptides is the stimulation of protein serine/threonine phosphorylation, due to the activation of several protein serine/threonine kinases. In recent years, attention has been focused on one particular group of these kinases that appears to represent a common intermediate in many signal transduction pathways because the kinases have been found to be stimulated by a wide variety of extracellular signals (i.e., including insulin, EGF, PDGF, NGF, serum, PMA, nicotine, okadaic acid, dibutyryl cAMP, and bradykinin), in numerous types of cells including epithelial, neural, and immune cells). The latter group of protein kinases is variably referred to as microtubule-associated protein-2 kinase (1, 2), myelin basic protein (MBP) kinase (3), mitogen-activated protein (MAP) kinase (4), and extracellular signal-regulated protein kinases (ERKs (5)), as well as by other names (for a review see citations 6–8). One form of the enzyme (ERK1) has reportedly been purified (9), and its cDNA sequence has been reported (5). Other isozymes may also be present in mammalian tissues, as well as in other organisms (7, 10). Accumulating evidence suggests that MAP kinases play an important role in cellular signaling by phosphorylating a wide variety of important substrates, including regulatory proteins such as c-jun (11), c-myc (12), Raf-1 (13), and the EGF receptor (14); dendritic axonal process substrates involved in microtubule rearrangement for neurite outgrowth (67); $pp90^{rsk}$ ribosomal S6 kinase (15–17); and bradykinin (21) a G-protein-linked signal transduction.

Several models have been proposed for the mechanism of action of the MAP kinase activator(s) (19–22). These include the possibility that the MAP kinase activator(s) is a single protein kinase that catalyzes the phosphorylation of both tyrosine and threonine residues or that it is a kinase that catalyzes the phosphorylation of only one of these residues, and this is then followed by autophosphorylation of the other. Another possibility is that the MAP kinase activator(s) is not a kinase but is a protein factor that increases the rate of autophosphorylation of MAP kinase on tyrosine and threonine residues. The last possibility was supported by the observation that ERK1 and ERK2 are capable of autophosphorylation on tyrosine and threonine residues (22–25), a reaction that is accompanied by autoactivation (22,25), and by the fact that no substrates for the MAP kinase activator(s) other than MAP kinase has been detected (19).

Two forms of MAP kinase activating proteins have been reported in Swiss 3T3 cells. These activating proteins, which were present in their active forms only after EGF stimulation of the cells, promote phosphorylation of MAP kinases on threonine and tyrosine residues (19). In addition to their activation by EGF, the MAP kinase activators appear to be stimulated by phorbol esters (19) and possibly related components have been identified in PC12 cells (20,21), where they are activated by nerve growth factor or bradykinin (21). The ability of the MAP kinase activators to be activated by the various factors suggests that they may play an important role in the growth factor-stimulated kinase cascade (19).

SUMMARY OF THE INVENTION

Mitogen-activated protein kinase (MAPK) activator has been purified greater than 2000-fold, sequenced, cloned, and its functional activities defined. Purified MAPK activator exhibits protein kinase activity with restricted substrate specificity for MAPK substrates, i.e., it is a MAPK kinase (or MAPKK). Two forms of MAPKK (termed MAPKK1a/MAP activator type 1; and, MAPKK1b/MAP activator type 2) were purified by sequential chromatography on Q-Sepharose, heparin-agarose, hydroxylapatite, ATP-agarose, Sephacryl S-300, Mono-S, and Mono-Q. As purified, the two forms both have MAPKK enzymatic activity and apparent molecular masses of 46 kDa and 45 kDa on sodium dodecyl sulfate-polyacrylamide gel electrophoresis. Using inactive mutants of MAP kinase as potential substrates, it was found that MAPKK1a and MAPKK1b both catalyze phosphorylation of the regulatory residues, threonine 188 and tyrosine 190, of Xenopus MAP kinase substrate. MAPKK1a and MAPKK1b also both demonstrate an apparent high degree of specificity toward the native conformation of MAP kinase substrates, although slow autophosphorylation on serine, threonine, and tyrosine residues and phosphorylation of myelin basic protein on serine and threonine residues was detected as well.

Cloning of MAPKK1a and MAPKK1b confirmed the presence of two distinct forms of cDNA that encode two different proteins within the same human T-cells. MAPKK1a is a protein kinase enzyme with a calculated molecular weight of 43,439 Da (based on the residue weight of amino acids in the sequence), while MAPKK1b has a calculated molecular weight of 40,745 Da. Analysis of the MKK1b nucleotide sequence strongly suggests that MAPKK1b protein results from an alternatively spliced form of the MKK1 gene. Northern analysis revealed that the MKK1 cDNA hybridizes with a single 2.6 kb mRNA species in all human tissues examined. Sequence comparison shows homology to a group of yeast kinases that participate in signal transduction and to subdomain XI of other dual specificity kinase.

DETAILED DESCRIPTION OF THE PREFERRED EMBODIMENT

Abbreviations used herein include: EGF, epidermal growth factor; MAPK, mitogen activated protein kinase; MAPKK and MAPK kinase are used interchangeably for mitogen activated protein kinase kinase; MKK, for mitogen kinase kinase nucleic acids capable of encoding MAPKK; PCR, polymerase chain reaction; MBP, myelin basic protein; DTT, dithiothreitol; MAP, mitogen-activated protein; ERK, extracellular signal-regulated protein kinase; BSA, bovine serum albumin; SDS-PAGE, polyacrylamide gel electrophoresis in the presence of sodium dodecyl sulfate; EGF, epidermal growth factor; FFQ, fast flow QSepharose; and, cAMPdPK, cAMP-dependent protein kinase, catalytic subunit.

A signal transduction pathway has been identified in recent years that leads to the artivation of a serine/threonine protein kinase cascade. Three enzymes in this pathway have been identified: the pp90 ribosomal S6 kinase ($pp^{90rsk}$); the mitogen-activated protein kinase, also referred to as microtubule associated protein-2 kinase, myelin basic protein kinase, or extracellar signal regulated kinase (ERK); and the MAP kinase-activator, also referred to as MAP kinase kinase (MAPKK). In vitro studies now suggest that these enzymes form three successive tiers of a protein kinase cascade in which MAP kinase activator phosphorylates and activates MAP kinase, and MAP kinase phosphorylates and activates $pp^{90rsk}$. The present disclosure is focused upon the MAPKK protein, its purification, amino acid sequence, and functional domains; and, upon the nucleotide sequences that encode MAPKKs in cells. The results presented in Example 1 show purification of MAPKK from cellular extracts in a six step procedure requiring four steps of ion exchange chromatography, two steps of affinity exchange chromatography, and molecular-sieve chromatography. For effective purification to substantial homogeneity it was found necessary to protect the activity of the enzyme with a carrier (i.e., Triton X-100 at less than the critical micellar concentration) as the enzymes were unstable and rapidly lost activity, and to maintain enzyme-associated $Zn^{++}$. Purification of MAPKK protein by greater than 10,000-fold allowed (for the first time) the determination that the protein is a protein kinase enzyme with specificity for MAP kinase substrates. As described in the Examples 1–5, below, the purified human MAPKK enzyme exists as two related polypeptides having apparent molecular weights on SDS-12% PAGE of 46 kDa and 45 kDa. The most likely relationship between these two different sizes of MAPKKs was revealed (as described in Examples 6–11), by molecular cloning and nucleotide sequence analysis, to be as proteins deriving from alternative splicing of a single gene. Regions of the MAPKK amino acid sequence show homology with other protein kinases, however, MAPKK shows homology with MAPK only in a small part of the kinase domain and there is little overall homology at either the amino acid level or nucleotide level between MAPK and MAPKK. Purification of MAPKK1a and MAPKK1b and functional characterization of these important signal transduction enzymes are described in the First Series of Examples (Examples 1–5), molecular cloning of the cDNA is described in the Second Series of Examples (Examples 6–11), and genomic cloning and expression systems are described in the Third Series of Examples (Examples 12–13), below.

As used herein the terms below are intended to have the following meanings:

"MAPKK1" is intended to mean mitogen activated protein kinase kinase type 1, and includes both MAPKK1a (SEQ ID NO:33) and MAPKK1b (SEQ ID NO:35).

"MAPKK1a" is intended to mean MAPKK type 1a, as shown in SEQ ID NO:33 (and illustrated in Example 6, below).

"MAPKK1b" is intended to mean MAPKK type 1b, portions of which are shown in SEQ ID NO:35 (and illustrated in Example 3, below).

"MKK" is used to mean an isolated nucleic acid capable of encoding at least a portion of an MAPKK1a, MAPKK1b, or MAPKK2 protein.

"MKK1" is used to mean an isolated nucleic acid capable of encoding at least a portion of an MAPKK1a and/or MAPKK1b protein. Illustrative examples of MKK1 DNA include genomic DNA with exon and intron nucleotide sequences (e.g., cloned genomic cosmid DNA, and the like). In one representative example MAPKK1a and MAPKK1b proteins result from alternative splicing of mRNAs from MKK1 genomic DNA.

"MAPKK2" is intended to mean MAPKK type 2 encoded by MKK2 RNA that is a 5.5 kb mRNA detectable in human brain, liver, and kidney by hybridization under stringent conditions with at least a portion of the nucleotide sequence of SEQ ID NO:32 or SEQ ID NO:34. Illustrative methods for detecting MKK2 may be found in Example 8, below.

The term "nucleic acid" is used herein to refer to natural or synthetic + and/or – strands of DNA, RNA, polynucleotides, or polynucleosides (i.e., greater than three nucleotides or nucleosides), and synthetic or natural oligonucleotides (i.e., greater than nine nucleotides or nucleosides), including antisense RNA and oligonucleotides.

The term "capable of specifically hybridizing" is used interchangeably with the term "capable of hybridizing under stringent conditions" herein to mean that members of the subject group of nucleic acids may be readily identified by their ability to hybridize under stringent conditions with all or parts of an isolated DNA segment that is contained in an MKK nucleotide sequence found in SEQ ID NO:32 and SEQ ID NO:34. Isolated DNA segments consist of nucleotide sequences that, in turn, may be used to construct (or isolate) a variety of nucleic acid molecules (i.e., cDNA, RNA, synthetic and natural polynucleotides, oligonucleotides, antisense oligonucleotides, and the like). Nucleic acids that are members of the subject group of molecules are rapidly identified by their common capacity to hybridize under stringent conditions with the subject isolated DNA segment containing the MKK nucleotide sequence. The nucleic acid molecules that are so capable of hybridization commonly contain a nucleotide sequence that is complementary with at least one helical turn (about 10 to 15 nucleotides) of a + or – strand of the subject isolated DNA segment. By capable of hybridizing under stringent conditions it is meant that annealing the subject nucleic acid with at least a region of a genetic marker occurs under standard conditions, e.g., high temperature and/or low salt content, which tend to disfavor hybridization of noncomplementary nucleotide sequences. A suitable protocol (involving 0.1×SSC, 68° C. for two hours) is described in Maniatis, T., et al., Molecular Cloning: A Laboratory Manual, Cold Springs Harbor Laboratory, 1982, at pages 387–389. Such hybridizing nucleic acid molecules may be related to the disclosed sequences by deletion, point mutation, base substitution, frameshift, alternative ORFs, mRNA splicing and processing, or post-transcriptional modification (e.g., methylation and the like).

The term "MKK nucleotide sequence" is used herein to refer to a contiguous nucleotide sequence of greater than about nine nucleotides found in the nucleotide sequence of SEQ ID NO:32 and SEQ ID NO:34.

The term "contiguous nucleotide sequences" is used herein to refer to a sequence of nucleotides linked in a serial array, one following the other.

The term "PCR" is used herein to refer to the process of amplifying DNA segments through the use of a DNA template molecule, two oligonucleotide primers, and a DNA polymerase enzyme. The DNA template is dissociated at high temperature from primers that may be annealed to the template. The DNA polymerase copies the template starting at the primers. The process is repeated 30–40 times to amplify and enrich the template-specific molecules in the reaction product.

"Isolated DNA segment" is used herein to refer to a DNA fragment, such as a cDNA, or a PCR amplified chromosomal DNA segment containing at least a portion of a MKK nucleotide sequence. The subject isolated DNA fragments may be identified by Southern blotting (e.g., for fragments), e.g., using probes capable of hybridizing with a nucleotide sequence in SEQ ID NO:32 and SEQ ID NO:34, which may allow identification of isolated DNA segments that differ by as little a one base pair.

The term "expression vector" is intended to mean an isolated nucleic acid segment capable of directing trancription and translation of an MKK nucleotide sequence in a host cell. The subject expression vectors include vectors capable of transforming the subject genetic information contained within the isolated DNA segments into bacterial (e.g., pBR322, pUC118, Bluescript, M13, and the like) and yeast cells (e.g., YAC, and the like), as well as those vectors capable of directing expression in mammalian host cells, e.g., vital vectors (e.g., retroviral vectors, adnenovirus vectors, HSV vectors, CMV vectors, SV40 vectors, polyoma vectors, Epstein Barr Virus vectors, and the like).

"Transforming" a host cell is intended to mean the process of transducing (i.e., through infection) or transfecting (i.e., through physical methods such as calcium phosphate) the subject isolated DNA segment into a host cell to derive a genetically-recombinant host cell.

The term "host cell" is intended to mean bacterial, yeast, and mammalian cells capable of transformation with the subject expression vectors.

The term "substantially purified protein preparation" is intended to mean an MAPKK protein preparation having a purification factor greater than about 50-fold, preferably greater than about 500-fold, and most preferably greater than about 5000-fold. The fold-purification of an MAPKK protein preparation may conveniently be determined as illustrated in Example 1, below (Table 3), or, alternatively, by electrophoresis of the subject protein preparation and appropriate control preparations on 8%, 10%, or 12% SDS-PAGE under nonreducing or reducing conditions, followed by staining of protein bands with Coomassie Brilliant blue and peak quantitation by optical scanning densitometry.

Those skilled in the art will recognize that the substantially purified MAPKK proteins of the invention (e.g., SEQ ID NO:33 and SEQ ID NO:35) are useful in a variety of applications, including at least two illustrative types of assays described below. First, MAPKK proteins (i.e., from recombinant sources and/or substantially purified from natural sources) are useful as substrates in assays for isolating and cloning novel MAPKK-activator proteins (i.e., proteins other than Raf-1 that activate MAPKK enzyme activity), and novel regulatory proteins that "modulate" MAPKK activity on an MAPK substrate. In the latter case, modulate is intended to mean that the subject regulatory proteins may: a) increase or decrease a measured enzyme activity such as Km, $V_{max}$, turnover number, and the like; or, b) may bind to MAPKK to form regulatory complexes, wherein an MAPKK enzyme activity is increased or decreased; or, c)the stability of the enzyme is increased or decreased (i.e., the measured enzymatic half-life of the enzyme); or, d) may enzymatically inactivate the subject MAPKK enzyme. The phosphorylation assays described in the Examples (below) are illustrative of the types of assays that may be used to identify and clone proteins that "modulate" the activity of an MAPKK enzyme on an MAPK substrate.

Second, the subject MAPKK proteins are useful in screening assays for identifying chemical inhibitors (or enhancers) of MAPKK enzyme activity that are candidate agents for inhibitors (or enhancers) of signal transduction pathways in cells. The "term signal transduction pathways" as used herein is intended to mean the series of events triggered at the plasma membrane following binding of ligands to specific membrane receptors (e.g., growth factors/ receptors) or following interaction of membrane active agents such as PMA. The subject signal transduction pathways may be mediated through a variety of second messengers, including for example: tyrosine kinases, Protein Kinase C, calcium, diacyl glycerol, phosphoinositides, G-proteins, cyclic nucleotides and others. In one such screening assay, the effect of a chemical agent on the MAPKK enzyme activity may be tested by adding it to a suitable incubation mixture of an MAPKK enzyme and an MAPK substrate, e.g., in a phosphorylation assay such as one of those illustrated in the Examples (below).

The isolated nucleic acids of the invention (e.g., isolated cDNAs, genomic DNAs, and RNAs, and portions thereof), are capable of hybridizing under stringent conditions with the MKK1a or MKK1b nucleotide sequences shown in SEQ ID NO:32 and SEQ ID NO:34, respectively. Skilled artisans will recognize that the isolated nucleic acids have a variety of uses including, for example: a) cDNA probes and oligonucleotide probes, e.g. for cDNA and genomic DNA cloning of other putative members of the MKK gene family in man, and including cloning of members of the gene family in other eukaryotic and procaryotic organisms; b) as probes for assaying the levels of MKK expression in a cell; c) as nucleic acids for constructing a variety of recombinant vectors (e.g., plasmids, cosmids, retroviral vectors, and the like); and d) as probes for in situ hybridization to identify the chromosomal location of the MKK and possible rearrangements of the MKK gene (including the gene regulatory region) in cancer and other cells. Illustrative examples of oligonucleotides capable of hybridizing with the nucleotide sequence of SEQ ID NO:32 and SEQ ID NO:34 are provided in Table 1, below. The subject examples of oligonucleotides are particularly useful as PCR primers and probes (e.g., in Southern and Northern analyses).

TABLE 1

| Oligonucleotide Probes and PCR primers for MKK1 | | | |
|---|---|---|---|
| Sense | SEQ. ID. NO. | Antisense | SEQ. ID. NO. |
| ACGCCTATTCAGTTGAAC | 1 | TGGTCCCGTTAACTGCAG | 7 |
| GATGACGACTTTGAGAAG | 2 | GCCAGAAGGCTTGTGGGA | 8 |
| CAATCCGGAACCAGATCA | 3 | AGCCCACGATGTACGGA | 9 |
| GTCAGCGGGCAGCTCATC | 4 | GATGAGCTGCCCGCTGAC | 10 |
| CGACCTCCCATGGCAATT | 5 | AATTGCCATGGGAGGTCG | 11 |
| CCCGGTGGTTTGCCATGT | 6 | ACATGGCAAACCACCCGGG | 12 |

Skilled artisans will recognize, for example, that the subject isolated MKK DNA segments of the invention are useful for constructing at least cDNA cloning vectors, expression vectors, and cosmid cloning vectors useful for introducing the subject MKK DNA into bacterial cells, yeast cells, and mammalian cells. The subject vectors may contain the subject DNA segment operably-linked (i.e., in reading frame) with a promoter element, transcription regulatory control elements, elements suitable for transfection or transduction of the MKK DNA into the genomic DNA of the cell, elements useful for regulation of gene expression of the MKK DNA in the DNA of the cell, elements useful for efficient nuclear transport in mammalian cells, and/or elements useful for efficient synthesis and secretion by bacterial or yeast cells. In this case, vectors may contain regulatory control elements suitable for high-level transcription and/or high-level expression of an MAPKK protein in a transfected or transduced host cell.

The subject nucleic acids of the invention provide probes for measuring expression of MKK genes in cells. Since MAPKK places a central role in multiple signal transduction mechanisms, it is considered likely that the levels of MKK expression within a cell may reflect an average value of the ongoing traffic in intracellular signal transduction mechanisms. Thus, it it thought likely that actively prolifering cells, maturing cells, or differentiating cells may express different levels of MAPKK proteins, and have different levels of MKK expression, than resting stationary-phase cells. Further, it is thought possible that MKK expression may be greater in malignant cells (e.g., metastatic cells) than in their normal tissue counterparts. Thus, the subject MKK nucleic of the invention provide reagents useful in determining a premalignant state of a cells, i.e., by measuring the nascent steady-state level of signal transduction in a cell and comparing the level to normal counterparts of the cell, an increased level of expression may suggest that the cell has the potential to become a malignant cell.

The subject nucleic acids of the invention provide vectors for construction of recombinant host cells, i.e., transformed with the subject MKK nucleic acids of the invention and include bacterial, yeast, and mammalian cells. Skilled artisans will recognize that the subject transformed host cells are useful as a source of MAPKK1a, MAPKK1b protein, isolated MKK nucleic acids (e.g., MKK DNA or RNA), or as test cells in a variety of screening assays. The latter cellular screening assays are useful for identifying candidate agents that alter expression (i.e., at the transcription or translation level) of an MKK nucleic acid in a cell (i.e., DNA or KNA). Test agents that decrease the level of expression of an MKK nucleic acid in a cell may be candidate agents capable of inhibiting signal transduction, e.g., mediated by growth factors in cancer or vascular smooth muscle cells (e.g., candidate anticancer agents or anti-coronary arterial sclerosis agents, respectively), neuropeptides in neural cells (e.g., anti-depressant agents and the like), antigen triggering of immune T- and B-cells receptors (e.g., immunosuppressive factors and the like), and AIDS-related immunosuppression. Test agents that increase the level of expression of an MKK nucleic acid in a cell may be candidate agents capable of promoting signal transduction, e.g., mediating more rapid growth, maturation, or differentiation in cells (e.g., during wound repair, liver regeneration, weight gain in food animals and domestic animals, neuron growth, and the like).

The subject MAPKK proteins and peptides of the invention provide antigens (as illustrated in the Examples below) for preparing MAPKK-specific binding partners specific for epitopes within the MAPKK1a or MAPKK1b protein. The term "binding partners" as used herein is intended to mean immunoglobulin (e.g., IgM, IgG, IgA, IgD, IgE), fragments of immunoglobulin (e.g., F(ab')$_2$, Fab', Fab, Fc, CDR regions of Ig), and the like derived either from preparations of polyclonal or monoclonal cell populations, or from the product of a cell, e.g., recombinant bacterial, mammalian, yeast, or insect cells producing a portion of an Ig. The subject MAPKK-specific binding partners of the invention are, in turn, useful in a variety of solid-phase and liquid-phase immunoassay formats for detecting the presence or amount of an MAPKK protein in a biological sample (e.g., radioimmunoassays, enzyme-linked immunoassays, fluorescence immunoassays, and the like (e.g., in a microtiter plate format, on beads, or tubes, or other carders, and in a competitive or noncompetitive assay format involving separating "bound" from "free" antigen [or antibody], or in a simultaneous assay format). In an example of such a immunoassay the presence or amount of an MAPKK in a biological sample may be determined by contacting the binding partner with the biological sample, separating the bound from the free antigen, and then detecting the presence or amount of the bound antigen (or antibody). The subject assays may be useful for determining the presence (or amount) of one particular normal (or mutant) form of an MAPKK in a sample, and such a determination may provide useful information to assess the nascent level of intracellular signal transduction ongoing in a cell, tissue, organ, or hyperplastic mass (e.g., a benign or malignant cell mass).

The subject nucleic acids of the invention that are capable of hybridizing with the nucleotide sequences of SEQ ID NO:32 and SEQ ID NO:34, include DNA, RNA, and oligonucleotide probes encoding human MKK2. MKK2 nucleic acid is recognizable as 5.5 kb mRNA detectable in human brain, liver, and kidney by hybridization under stringent conditions with at least a portion of the nucleotide sequence of SEQ ID NO:32 and SEQ ID NO:34 (i.e., as illustrated in Example 9, below).

FIRST SERIES OF EXAMPLES

The Figures noted below in this first series of examples, Examples 1–5, refer to the Figures reported in Seger et at., The Journal of Biological Chemistry 67(20):1473–1481, 1992 ("Seger et at., 1992a"), which is incorporated by reference herein. A description of the materials and methods referred to in this first series of examples follows Example 5.

EXAMPLE 1

Characterization of Crude MAP Kinase Activator from A431 Cells

In a previous paper the inventors showed the possible existence of MAPK activator activities in EGF- or PMA-stimulated Swiss 3T3 cells, that might function either as enzymes, or as proteins activating autophosphorylation of MAPK. In the following examples, the MAPK activator protein was substantially purified, sequenced, cloned, and functionally characterized. The following examples show the MAPK activator to be the kinase enzyme now termed MAPKK.

To identify starting material for protein purification of MAPK activators, several different cell lines were screened and human epidermal carcinoma A431 cells were found to be a particularly rich source of MAPK activator. In order to compare the MAPK activators from A431 cells with those discovered in the Swiss 3T3 cell line, confluent A431 cells were stimulated with 100 ng/ml EGF for 5 min, and cytosolic extracts from these cells were chromatographed on a 2-ml FFQ column. The eluted fractions were preincubated with or without inactive MAPK (see below, "Materials and Methods", following Example 5) in the presence of $Mg^{++}$ and ATP, and stimulation of activity toward MBP was assayed as described (FIG. 1A). Two peaks of MAPK activator were detected, eluting in the flow-through and at 0.05M NaCl. Extracts of unstimulated A431 cells did not show the presence of any MAPK activator activity (FIG. 1A). No significant phosphorylation was observed when MBP was omitted from the assay, indicating that the observed phosphate incorporation is not due to phosphorylation of endogenous proteins (data not shown).

To further characterize these MAPK activators, the separated peaks from FFQ were concentrated and chromatographed on Superose 12 (FIG. 1B) and Mono S (data not shown). The two peaks gave similar chromatographic profiles on each column, closely resembling those seen with EGF-stimulated Swiss 3T3 cells (20). The time course of activation (FIG. 1C) showed a peak at 5 min, and the dose response to EGF (FIG. 1D) showed maximal stimulation at >30 ng/ml EGF. Since A431 cells appeared to contain 10-fold more MAPK activator/plate of confluent cells than Swiss 3T3 cells, the former were chosen for further purification of the MAPK activator 2.

The results presented in FIG. 1 show an overview of the purification and functional activities of purified MAPK activator from A431 cells. In FIG. 1A the results are shown for fractionation of MAPK activator from EGF-stimulated and nonstimulated A431 cell extracts by anion exchange chromatography. In these experiments A431 cells (three plates, $2 \times 10^6$ cells) were incubated for 5 min with (closed circle; ●) or without (open circle; ○) EGF (100 ng/ml) and harvested as described under Materials and Methods, below, following Example 5. Cytosolic extracts of these cells (prepared without freezing) were fractionated on a 2 ml FFQ column using an increasing NaCl gradient (indicated by the broken line) in Buffer E (flow rate of 1 ml/min), and 1 ml fractions were collected. Aliquots of every other fraction were tested for MAPKactivation as described. In FIG. 1B, the results of fractionation of MAPKactivators by gel filtration are shown. In these experiments, Peaks 1 (closed circle; ●) and 2 (open circle; ○) from a similar experiment to that shown in FIG. 1A were concentrated using a Microprodicon apparatus. Then, 250 µl of each peak (total of 2800 units of peak 1 and 3900 units of peak 2) were loaded on an fast protein liquid chromatography sizing column Superose 12 (flow rate 0.3 ml/min, and 0.3-ml fractions were collected. The fractions were assayed for MAPKactivator by the activation assay (see "Experimental Procedures"). The positions for the elution of thyroglobulin (667 kDa), IgG (150 kDa), ovalbumin (44 kDa), and myoglobin (17 kDa) are indicated in the Figure. In FIG. 1C, the results are shown of a time course study of stimulation of MAPK activator activity in A431 cells that were either incubated with (closed circle; ●) or without (open circle, ○) EGF (100 ng/ml) for the indicated periods of time, after which time the cells were harvested, and the specific activity of the MAPK activator was determined after fractionation as described under Materials and Methods, below (estimation of MAPKactivator activity in cytosolic extracts). Each time point represents an average of two plates ($1.5 \times 10^6$ cells) except for the 5-min point which is the average of four plates. In FIG. 1D, the results are shown of dose-response studies for stimulation of MAPK activator by EGF. In these experiments A431 cells were treated with the indicated concentration of EGF for 5 min, after which they were harvested, and the specific activity of the MAPKactivator was determined as in FIG. 1C. Duplicate plates ($1.5 \times 10^6$ cells) were tested in each concentration.

EXAMPLE 2

Purification and Characterization of MAPKActivators

Purification of the MAPK activator(s)

Two assays were used to measure the MAPK activator activity throughout the purification. One of the assays was based on the activation of inactive MAP kinases obtained from nonstimulated Swiss 3T3 cells (B3). The other assay was based on the phosphorylation of the inactive MAP kinase, ERK2, present in B3 (see "Materials and Methods" following Example 5).

The description of purification of MAPK activator is described in overview in the following several paragraphs, followed in the next several paragraphs by a detailed description of the several Figures (again, as shown in Seger et al., 1992a, supra) that show the remits of each purification step.

In a typical preparation of MAPK activator(s) 500 plates ($4 \times 10^{10}$ cells) of A431 cells were stimulated by EGF at a concentration of 100 ng/ml for 5 min. Cytosolic extracts (usually 1.8 grams of total protein in 220 ml) were loaded onto a 400 ml FFQ column equilibrated with Buffer H (3 ml/min). The column was washed with 500 ml of Buffer H, and proteins were eluted with an increasing gradient of NaCl in Buffer H (0.0–0.3M NaCl, 1800 ml), into 12 ml fractions. Two peaks of MAPK activator were obtained, one eluting at 0.03M and the other at 0.08M NaCl; these were completely separated from the peak of MAPK (FIG. 2A). Both peaks of MAPK activator bound to the FFQ resin, whereas in FIG. 1, and in the previous paper (20), the first peak eluted in the flow through. This difference in elution profiles could reflect the properties of the resins (Mono Q vs FFQ) or the column buffers (Buffer H vs Buffer E). The first peak (fractions 43–68, 300 ml) and the second peak (fractions 69–85, 180 ml) were termed Peak 1 and Peak 2 and were purified in parallel.

Peak: 1 (from above) was loaded (2 ml/min) without further dilution onto a 180 ml heparin agarose column, prewashed with Buffer A. Peak 2 was first diluted with 90 ml of Buffer H before being handled in the same manner. In each case, the column was washed with 250 ml of Buffer A and proteins were eluted with increasing 5 NaCl gradient (0.0–0.25M NaCl in (600 ml, 2.5 ml/min), and collected in 5 ml fractions. Both Peaks 1 and 2 were eluted as one peak at around 0.15M NaCl (FIGS. 2B and 2C). Fractions 66–90 (120 ml) from each peak were then pooled and loaded onto a 20 ml hydroxylapatite column prewashed with Buffer A. The columns were washed with 25 ml of Buffer A and proteins were eluted with increasing phosphate gradients (0.0–0.5M phosphate, 180 ml, 2 ml/min), and collected in 5 ml fractions. Peak 1 and 2, both fluted at 0.1M $K_2HPO_4$ (FIGS. 2D and 2E). Fractions 7–17 (55 ml) were pooled, dialysed each against Buffer A, and concentrated (Microprodicon apparatus) to a final volume of 1 ml.

Next, each pool was passed (0.5 ml/min) over a 2 ml ATP agarose column (not illustrated) prewashed with Buffer A and the columns were further washed with 10 ml of Buffer A. The flow through material and the wash were collected in 1 ml fractions. Usually, >85% of the activity of both MAPK activators from Peaks 1 and 2 were eluted in the first five fractions, which were then pooled and loaded onto a 180 ml Sephacryl S-300 column (200×1 cm, 1.2 ml/min) equilibrated in Buffer C, 3 ml fractions were collected. Each peak of MAPK activator resolved (FIG. 2F; FIG. 2G) into a main peak (60%) eluting with molecular mass of around 50 kDa and a broad shoulder in which the peak fraction eluted at molecular mass of 220 kDa for Peak 1 and 100 kDa for Peak 2. When the broad shoulders were concentrated and reloaded on the same column under the same conditions, a similar profile of two peaks was obtained (data not shown). These results suggest that some sort of equilibrium may exist between the higher and the lower molecular weight forms. With Peak 1, another high molecular weight phosphorylating activity was detected (FIG. 2F), however, no activation could be observed in this fraction indicating that this phosphorylation is probably due to an unidentified kinase. Only the main peak (50 kDa) was used for further purification.

A detailed description follows for the Figures (in Seger et al, 1992 Supra) which show the results of the purification steps. The results presented in FIG. 2 show the purification of MAPK activators 1 and 2. A431 cells (500 plates, $4\times10^{10}$ cells) were treated with EGF (100 ng/ml) for 5 min after which the cells were harvested in Buffer H, centrifuged (100,000×g, 20 min), and the supernatants were kept at −70° C. The extracts were thawed, recentrifuged for 50 min at 100,000×g, and the supernatant was fractionated by anion exchange chromatography on a FFQ column. Fractions were assayed for MAPKactivator activity using activation (closed circle; ●) or phosphorylation (open circle; ○) assays described in Experimental Procedures (the results of both assays were superimposed by equating the maximal activity obtained by each method). MAPKactivity (heavy bar in FIG. 2A) was measured by a filter paper assay, and protein concentration (- - -) was determined by the Bradford assay. The two peaks (1 and 2) were pooled separately and each subfractionated individually using chromatography on heparin agarose (FIG. 2B and FIG. 2C), hydroxylapatite (FIG. 2D and FIG. 2E), ATP agarose (not illustrated), Sephacryl S-300 (FIG. 2F and FIG. 2G) and Mono S (FIG. 2H and FIG. 2I). Peak 1 purification is shown on the left and Peak 2 results on the right. Further details of the purification are covered in the text. The positions for the elution of molecular weight standards (described in FIG. 1) on Sephacryl S-300 column are shown in FIGS. 2F and 2G. The increasing salt gradient ([M]) in the appropriate columns is indicated. In all cases, no MAPKactivator activity could be detected in the flow through the columns (not shown). Activity from the Sephacryl S-300 columns (fractions 69–78, 30 ml) was loaded onto a 1 ml Mono S HR 5/5 column (1 ml/min), equilibrated with Buffer C. The column was washed with 5 ml of Buffer C, proteins were eluted by an increasing NaCl gradient in Buffer C (0.0–0.25M NaCl, 72 ml), and 1 ml fractions were collected. Peak 1 was eluted around 120 mM NaCl (FIG. 2H, whereas Peak 2 (FIG. 2I) eluted at around 30 mM. Peak fractions of the Mono S column (fractions 38–52 for Peak 1 and 10–25 for Peak 2, 15 ml each) were pooled, diluted with 7.5 ml of Buffer C and loaded onto a 1 ml Mono Q HR 5/5 column (1 ml/min) equilibrated in Buffer C. The column was washed with 10 ml of Buffer C, developed with a shallow NaCl gradient (0.0–0.15M, 48 ml) and 1 ml fractions were collected. Peak 1 was eluted mainly as one sharp peak at 40 mM NaCl concentration, although a smaller peak of activity was detected at approximately 120 mM NaCl (FIG. 3A). Peak 2 was eluted later in the gradient, around 130 mM NaCl, as a slightly broader single peak, although a small amount of an earlier peak was detected as well (FIG. 3B). The relative amounts of the smaller peaks, both in Peak 1 and Peak 2, varied from preparation to preparation and could reach up to 30% of the total activity. The reason for this separation is not clear as yet, but the reciprocal nature of the elution profiles of Peaks 1 and 2, together with the low MAPKactivator activity detected in the fractions between these separated peaks in each Mono Q column (FIGS. 3A and 3B) raises the possibility that Peak 1 and2 represent two interchangeable forms of the same protein. Although it is not clear whether the MAPKactivators from Peak 1 and 2 are distinct proteins, we will refer to them in Examples 1–5 as MAPKactivators 1 and 2. (Results presented in the Second Series of Examples, i.e., Examples 6–11, below, confirm that these activators have kinase activity, and should properly be termed MAPKkinase enzymes.)

The results presented in FIG. 3 show fractionation of MAPK activators 1 and 2 on a Mono Q column. In FIG. 3A, the pooled fractions from the Mono S column of Peak 1 (FIG. 2H) were loaded onto Mono Q HR 5/5 column that was developed by an increasing NaCl gradient (. . .). Further details of the chromatography are in the text. MAPKactivator was measured by the activation (closed circle; ●) and phosphorylation (open circle; ○) assays (Experimental Procedures) and protein concentration (- - -) was determined by the Bradford assay. Aliquots from the peak fractions (100 µl each) were separated on a 7–12% gradient SDS-PAGE. The silver stain of the polyacrylamide gel is shown in the bottom panel. In FIG. 3B, the pooled fractions of the Mono S column of Peak 2 (FIG. 2I) were loaded onto the same Mono Q column which was then processed as described in FIG. 3A. Aliquots from the peak fractions (250 µl each) were separated by a 12% SDS-PAGE and stained as described for FIG. 3A.

To determine the purity of the MAPKactivators at this stage, column fractions were applied to SDS-PAGE and visualized by silver staining. With Peak 1, a 46 kDa polypeptide band correlating with the peak of activity eluted in fractions 9–12. This band represented 70–90% of the total protein in these fractions in each of 5 different MAPKactivator preparations (FIG. 3A). With Peak 2, a 45 kDa polypeptide band correlating with the peak of activity eluted in fractions 39–43. A similar polypeptide band was observed also in fractions 37 and 38 where no MAPKactivator activity was present (FIG. 3B). This latter band might represent a different protein, copurifying with the MAPKactivator or, perhaps, a nonstimulated form of the MAPKactivator.

The MAPKactivators purified as above were unstable, particularly in the later steps. Although stability was increased slightly by including Triton X-100 and fresh DTT in all the buffers and by storing the proteins at 0° C., after the ATP agarose and Sephacryl S-300 steps the activity rapidly declined ($t_{1/2}$~3 days). The cause of the inactivation is not clear, but is probably not due to proteolysis, since the mobility of the 45 and 46 kDa bands were unchanged even after 3 months at 0° C., nor due to phosphatases, since no significant dephosphorylation occured as reported by Ahn et al. (1991). Concentrating the proteins up to 40 mg/ml also did not help to stabilize them, suggesting that its instability was not due to low protein concentration.

Apparent Molecular Size of MAPK activators on SDS-PAGE: 45 and 46 kDa

The purification schemes of MAPK activators 1 and 2 are summarized in Table 1. In each case the extent of purification is estimated to be 2500–3000-fold from the first column (FFQ). Although it was impossible to measure the MAPK activator activities in total cell homogenates or in the cytosolic extracts, we estimate (based on the separation of the peaks of activity from most of the proteins) that the FFQ step may provide at least 5-fold purification (FIG. 2A), so that the total purification is probably at least 12,000-fold. In order to compare the enrichment of activity to the enrichment of the 46 kDa polypeptide band of Peak 1, aliquots from pooled fractions of each purification step were subjected to SDS-PAGE and the proteins were visualized by silver staining. The 46 kDa band was clearly observed only after the Sephacryl S-300 column (FIG. 4), and its enrichment in the last three steps of purification correlated with the enrichment of MAPK activator activity (Table 2), suggesting that this protein is indeed the MAPK activator.

corresponding to Mr 44 and 40 kDa, respectively (FIG. 5B). Combining estimates of sedimentation constants, with estimates of Stokes radii from gel filtration, revealed true molecular weights of 47,200 and 44,500 for MAPK activator 1 and 2, respectively. These data are consistent with the identification of the MAPK activators as monomeric 46 and 45 kDa polypeptides.

TABLE 2

Purification of MAPK Activators 1 and 2

| Step | Protein (tot. mg) | Activity (total units) | Yield (%) | Specific Activity (units/mg × $10^{-3}$) | Purification (fold) |
|---|---|---|---|---|---|
| Peak 1 | | | | | |
| FFQ | 90 | 162,000 | 100 | 2 | 1 |
| Heparin agarose | 5.4 | 128,000 | 79 | 24 | 13 |
| Hydroxylapatite | 01.55 | 72,000 | 44 | 46 | 26 |
| ATP agarose | 0.84 | 78,000 | 48 | 92 | 51 |
| Sephacryl S-300 | 0.086 | 92,000 | 57 | 1,069 | 593 |
| Mono S | 0.021 | 46,600 | 29 | 2,219 | 1,151 |
| Mono Q | 0.006 | 27,200 | 17 | 4,533 | 2,518 |
| Peak 2 | | | | | |
| FFQ | 58 | 117,500 | 100 | 2 | 1 |
| Heparin agarose | 2.85 | 85,416 | 72 | 30 | 15 |
| Hydroxylapatite | 0.88 | 52,250 | 44 | 59 | 30 |
| ATP agarose | 0.44 | 58,500 | 49 | 133 | 66 |
| Sephacryl S-300 | 0.028 | 55,000 | 46 | 1,964 | 982 |
| Mono Q | 0.007 | 27,290 | 23 | 3,900 | 1,950 |
| Mono S | 0.0028 | 14,165 | 12 | 5,232 | 2,616 |

The results presented in FIG. 4 show silver staining of proteins separated by SDS-PAGE of fractions from the purification of MAPK activator 1. Aliquots from the following pools were separated by 12% SDS-PAGE followed by silver staining. Lane 1, cytosolic extract (4 µg); lane 2, FFQ step (1.5 µg); lane 3, heparin agarose step (1 µg); lane 4, hydroxyapatite step (0.8 µg); lane 5, ATP agarose step (0.6 µg); lane 6, Sephacryl S-300 step (0.1 µg); lane 7, Mono S step (0.1 µg); and lane 8, peak fraction of Mono Q step (0.08 µg). These results are from two similar preparations.

It should be noted that in all of the MAPKactivator purification steps after the heparin agarose step, the fold purification assayed by measuring the rate of phosphorylation of the inactive ERK2, was similar to the fold purification assayed by activation of MAPKactivity (The phosphorylation assay could not be applied in the earlier steps because of high background by other protein kinases). The phosphorylation (open symbols, FIGS. 2 and 3) also directly correlated to the profiles obtained by activation activity measurements (closed symbols, FIGS. 2 and 3) in the same steps, as would be expected from the fact that phosphorylation is required for activation (4,20).

In order to confirm that the 46 and 45 kDa polypeptides are the MAPKactivators 1 and 2, respectively, we examined their activities after separation by SDS-PAGE or sucrose density gradient centrifugation. MAPKactivator 1 from the heparin agarose column (5 nmol/min in 0.4 ml) was prepared in the absence of heat or reducing agent and applied to SDS-PAGE. Proteins were eluted from gel slices and analyzed for activity. A small mount of MAPK activator activity could be recovered from a portion of the acrylamide gel corresponding to molecular mass of 43–50 kDa (FIG. 5A), consistent with the elution of the 46 kDa polypeptide. In addition, FFQ pools from both peaks were each separated by 2–15% sucrose density gradient centrifugation. Peak 1 (activity) and Peak 2 (activity) migrated at 4% sucrose, The results presented in FIG. 5 show a determination of the molecular weight of the MAPKactivators. In FIG. 5A, separation of MAPK activator was accomplished using SDS-PAGE: MAPK activator, from the peak fraction of the heparin agarose column of MAPK activator 1 (300 ml 120 units), was loaded on an 8% SDS polyacrylamide mini gel that was prepared with 0.5% BSA. Prestained molecular weight standards (Biorad, shown in the upper part of the figure) were also loaded. After separation (50 volts at 4° C.), the gel was washed in Buffer A (3×1 h) followed by horizontal slicing. The gel slices were then homogenized in an Eppendorf tube in 500 ml of Buffer A and were shaken for 28 h at 4° C. after which they were centrifuged and the insoluble gel removed. MAPK activator activity was determined in duplicates by the activation assay (Experimental Procedures). The 0 line (- - -) represents the average of 2 gel slices that were cut from an area below the dye front and treated the same way.

In FIG. 5B, determination of molecular size was accomplished by separation of the MAPK activator on a sucrose gradient: MAPKactivator from the FFQ column Peaks 1 (closed circle; ●) and 2 (open circle; ○) were concentrated using a Microprodicon apparatus. The concentrated peaks (300 ml each, 800 units in Peak 1 and 400 units in Peak 2) were loaded onto a 2–15% 30 ml sucrose gradient and centrifuged using the Beckman SW-27 rotor. Molecular weight standards (two tubes) and a buffer control were also loaded. The sucrose gradients were centrifuged for 21 hours at 25,000×g at 4° C. After the run, 0.5 ml fractions were collected from the gradients and aliquots of the indicated fractions were tested for MAPKactivator activity using the activation assay. The position of the molecular weight standards (top of the Figure) was determined by separating the proteins of each fraction by 10% SDS-PAGE.

MAPKK activates a phosphatase-inactivated MAP kinase

As noted above, it is reported that phosphorylation of MAPK on threonine and tyrosine residues is required for full activation (4, 20, 21), and it has also been reported that the two peaks of MAPK activators from Swiss 3T3 cells strongly enhance the rate of phosphorylation of both residues as well as serine in small amounts (20). In agreement with the latter result, the purified MAPK activators were found to cause the phosphorylation of tyrosine and threonine residues of ERK2 in the "B3" fraction, although a small mount of serine phosphorylation was also observed (data not shown). The purified MAPK activators 1 and 2 were also tested using a preparation of MAPK(ERK1), purified from Rat 1 HIRCB cells (10). Each of the MAPK activators could activate the purified ERK1 that had been inactivated either by a serine/threonine-specific phosphatase, P2A, or by the tyrosine-specific phosphatase, CD45 (FIG. 6A). MAPK activator 1 with higher specific activity caused reactivation of ERK1 that was inactivated by either of the phosphatases or both of them together (FIG. 6B). As expected, upon phosphoamino acid analysis of ERK1 reactivated under similar conditions, phosphate was detected mainly on tyrosine when CD45 was used for ERK1 inactivation, mainly on threonine when P2A was used and equally on both threonine and tyrosine when both phosphatases were used (FIG. 6B). These data indicate that the purified MAPK activators catalyze both phosphorylation reactions.

The results presented in FIG. 6 show that MAPK activators 1 and 2 possess catalytic activity sufficient to reactivate phosphatase-treated MAPK(ERK1) substrate. In FIG. 6A, ERK1, purified from insulin-stimulated Rat 1 HIRCB cells, was treated (see Materials and Methods, below) with the serine/threonine-specific phosphatase, phosphatase 2A, (closed symbols in upper panel) the tyrosine-specific phosphatase, CD45 (closed symbols in lower panel), or incubated with each phosphatase buffer as a control (open symbols in both panels). The reactions were terminated by phosphatase inhibitors as described, and the inactivated ERK1 (45 µl) was incubated with 45 ul of the following: MAPK activator 1 (200 units/ml, solid circles ●, open circles ○), MAPK activator 2 (80 units/ml, closed square ■, open square □), and Buffer C alone (closed triangle ▲, open triangle △), in the presence of BSA (0.83 mg/ml) and [γ-$^{32}$P]ATP (2 cpm/fmol) in Buffer R (final volume of 135 µl) at 30° C. After the indicated times, aliquots were sampled (21 µl) and incubated with 4 µl of MBP (2 mg/ml) for 20 min at 30° C., after which the amount of phosphate incorporated to the MBP was determined by the filter paper assay as described. In FIG. 6B, ERK1 was treated with phosphatase 2A, CD45, both phosphatases, and phosphatase buffer as described. The activity after each treatment was examined by the filter paper assay (time 0, black boxes). Then, 16 µl of each reaction mixture were incubated with (stippled boxes) or without (gray boxes) 16 µl of MAPKactivator 1 (480 u/ml) in the presence of BSA (0.83 mg/ml) and [γ-$^{32}$P]-ATP (2 cpm/fmol) in Buffer K (final volume of 48 µl) at 30° C. for 10 min, after which the activity of the ERK1 toward MBP was determined as described in FIG. 6A. To determine the phosphoamino acid content after each treatment, 15 µl of each reaction mixture were incubated with 15 µl of the same MAPKactivator in the presence of [γ-$^{32}$P]ATP (20 cpm/fmol) in Buffer R (final volume of 45 µl) for 60 min at 30° C. The reactions were terminated by Laemmli sample buffer, and the phosphoamino acid content was determined as described under "Experimental Procedures."

EXAMPLE 3

The MAPK Activators 1 and 2 Are Protein Kinases

Partially purified preparations of MAPK activator failed to phosphorylate several known substrates for protein kinases (Ahn et al., 1991), and studies showing autophosphorylation of ERK1 and ERK2 on both threonine and tyrosine residues raised the possibility that the MAPK activator might not necessarily be a protein kinase (22). We therefore undertook to resolve this issue by examining the ability of the MAPK activator to phosphorylate forms of MAPK that were catalytically inactive.

Recently, expression of a *Xenopus* MAPK in reticulocyte lysate has been reported (28). This MAPK could be phosphorylated by partially purified *Xenopus* MAPK activator, and it has been shown that phosphorylation of either threonine 188 or tyrosine 190 reduces the mobility of the MAPK on SDS-PAGE (28). In addition to the wild type enzyme (WT), several mutants of the MAPK have been constructed, containing: substitution of the lysine residue that is involved in ATP binding to arginine residue (K57R), the regulatory threonine to valine (T188V), the regulatory tyrosine to phenylalanine (Y190F), and both threonine and tyrosine to valine and phenylalanine, respectively (TY/VF).

These mutants were tested as substrates for the purified MAPK activators. As determined by the shift in migration on SDS-PAGE (FIG. 7A), it appears that WT, K57R T188V, and Y190F could be phosphorylated by each of the MAPK activators. As expected, only the activity of the wild type MAPK (determined by phosphorylation of the fusion protein glutathione S-transferase-myc) was increased upon incubation with MAPK activators. This is consistent with the requirement for phosphorylation on both tyrosine and threonine residues, as well as an intact active site for full MAPK activity. To verify that the shift is due to phosphorylation, the K57R mutant was used as a substrate for the MAPK activators 1 and 2 in the presence of [γ-$^{32}$P] ATP. Phosphate incorporation into the K57R mutant was comparable with the wild type, and in each case, phosphorylation of threonine, tyrosine, and serine residues was detected. Given that the double mutant (TY/VF) was not phosphorylated, it seems that most of the phosphorylation of the threonine and tyrosine residues must be due to phosphate incorporation into threonine 188 and tyrosine 190; however, the nature of the serine phosphorylation is not clear. These results strongly indicate that both MAPK activators 1 and 2 are protein kinases that are able to phosphorylate serine, threonine, and tyrosine residues and therefore these kinases belong to a growing group of dual specificity protein kinases (22, 34–37).

The results presented in FIG. 7 show phosphorylation of modified forms of *Xenopus* MAPK by MAPK activators 1 and 2. In FIG. 7A, the following constructs of *Xenopus* MAPK were translated in a reticulocyte expression system using [$^{35}$S]methionine to label the proteins: wild type (WT), lysine 57 mutant (K57R), threonine 188 mutant (T188V), and tyrosine 190 mutant (Y190F). The proteins were immunoprecipitated, washed, and incubated in the presence of 1 mM ATP and 10 mM Mg$^{++}$ with 50 µl of MAPKactivators 1 and 2 (from the Sephacryl S-300 column, 4000 units/ml each) or Buffer control for 30 min at 30° C. The immunoprecipitates were washed, and [γ-32P]ATP (10 cpm/pmol) and the MAPKsubstrate, glutathione Stransferase-myc (GST-myc) were added for an additional 30 min. The radioactive proteins were separated by 10% SDS-PAGE followed by sting, destaining, and exposure to X-ray film. In FIG. 7B, in vitro translation of wild type *Xenopus* MAP kinase, lysine mutant (K57R), and a construct mutated on both threonine and tyrosine (TYVF) was performed as above in the absence of the [$^{35}$S]methionine. After immunoprecipitation and washing, MAPKactivators (200 units for each reaction, (+)) or Buffer control (-) were added in the presence of 20 μM [γ-$^{32}$P]ATP (20 cpm/fmol) for 30 min at 30° C. The reaction was terminated by boiling in Laemmli sample buffer and separated by 10% SDS-PAGE. The bands of the phosphorylated MAPK were excised from the gel and subjected to phosphoamino acid analysis. PY, phosphotyrosine; PT, phosphothreonine; PS, phosphoserine.

EXAMPLE 4

Substrate Specificity of the MAPK Activators

Since the above results demonstrate that the MAPK activators are protein kinases, we examined a group of proteins and peptides known to be phosphorylated by either protein serine/threonine kinases or by protein tyrosine kinases, for their ability to serve as kinase substrates for the MAPK activators. From the results in Table 3, it is clear that none of the substrates examined, except the native MAPK itself, was significantly phosphorylated by the MAPK activator, even at high protein concentrations (2 μg/ml). In particular, phosphorylation was not observed using heat-denatured MAPK (denatured at 55° C. for 12 min) or with peptide containing the MAPK phosphorylation sites (TEY peptide: PEHDHTGFLTEYVATRWYR). These results emphasize the apparent high degree of specificity of the MAPK activator which recognizes the native form of the MAPK as a substrate almost exclusively. However, very slight activity toward some substrates could be detected (Table 3). For example, MBP could also be phosphorylated by the purified MAPKactivators (FIG. 8A). This phosphorylation was probably by the MAPK activators themselves, because it correlated with MAPK activator activity in the last three column steps of the purification (data not shown). Phosphorylation of MBP was mainly on serine and to a lesser extent on threonine residues (FIG. 8B), suggesting that the site of phosphorylation is distinct from that phosphorylated by the MAPK(7).

TABLE 3

Substrate specificity of MAPK activators 1 and 2

| Substrate | Phosphorylation[a] Peak 1 nmol/min/mg | Peak 2 nmol/min/mg |
|---|---|---|
| Recombinant ERK2 (70 μg/ml)[b] | 150 | 60 |
| Recombinant ERK2 (50 μg/ml) | 12 | 7 |
| Heat-denatured ERK 2[c] | <0.01 | <0.005 |
| TEY peptide (1 Mm) | 0.04 | 0.005 |
| MBP (0.33 mg/ml) | 0.1 | 0.12 |
| Histones (0.5 mg/ml) | 0.02 | 0.04 |
| Protamine (0.33 mg/ml) | 0.01 | 0.03 |
| Casein (2 mg/ml) | <0.005 | <0.005 |
| Ribosomal S6 protein (0.3 mg/ml) | <0.005 | <0.005 |
| Denatured enolase (0.1 mg/ml) | <0.005 | <0.005 |
| pp90$^{rsk}$ (20 μg/ml) | <0.01 | ND[d] |
| ζS6 kinase (2 μg/ml) | <0.01 | ND |
| Raf-1 (2 μg/ml) | <0.01 | <0.01 |
| cAMPdPK (20 μg/ml) | <0.01 | ND |
| Poly(Glu$^{80}$-Ty$^{20}$)(1.5 mg/ml) | <0.01 | <0.005 |
| Kemptide (0.2 mM) | <0.005 | <0.005 |
| S6 peptide (0.25 mM) | <0.005 | 0.07 |
| Syntide-2 (0.25 mM) | <0.005 | 0.04 |
| RR-SRC (1 mM) | <0.005 | 0.005 |
| Bank 3 peptide (1 mM) | <0.005 | <0.005 |
| ETE peptide (1 mM) | <0.005 | <0.005 |

[a]MAPK activator 1 (60 units) and 2 (90 units) were used to phosphorylate the indicated substrates as described under "Materials and Methods", below;
[b]Same as Footnote "a" except the final volume was 1.5 ml, and MAPK activators 1 and 2 were 6000 and 3200 units, respectively.

TABLE 3-continued

Substrate specificity of MAPK activators 1 and 2

| Substrate | Phosphorylation[a] Peak 1 nmol/min/mg | Peak 2 nmol/min/mg |
|---|---|---|

[c]Heat-denatured ERK2 was prepared by heating 50 ul of the recombinant ERK2 (200 μg/ml) at 55° C. for 12 min, after which the concentration of proteins in solution remained unchanged. Its final concentration in the reaction was 70 μg/ml.;
"ND", not determined.

The results presented in FIG. 8 show characterization of phosphorylation reactions catalyzed by the MAPKactivators 1 and 2. In FIG. 8A, MAPKactivators 1 (6700 units/ml) and 2 (7000 units/ml), purified through the Sephacryl S-300 step were used in the following experiments. Lane I) Aliquots (12 μl) from each fraction were autophosphorylated as described under Experimental Procedures ([γ$^{32}$P] ATP—60 cpm/fmol, final volume 18 μl for 30 min). Lane II) Each fraction (10 μl) was incubated with 2 μl of the B3 fraction under the same conditions as above. Lane III) Each fraction (12.5 μl) was incubated with MBP (4.2 μl, 2 mg/ml) in the presence of [γ$^{32}$P] ATP (60 cpm/fmol) in Buffer R (final volume of 25 μl) for 20 min at 30° C. All the reactions were terminated by boiling in Laemmli sample buffer and separated by a 12% SDS-PAGE, followed by electrophoretic transfer onto Immobilon-P which was exposed to X-ray film. I and II are 36-h exposures and III is a 6-h exposure. The arrowheads represent (from top to bottom) MAPK activator 1, MAPK activator 2, ERK1 and ERK2. The 1 and 2 in the bottom represent MAPKactivators 1 and 2. In FIG. 8B, The relevant bands were excised from the Immobilon-P and subjected to phosphoamino acid analysis as described. (Peaks 1 and 2 are MAPK activators purified from the FFQ peaks 1 and 2).

EXAMPLE 5

Autophosphorylation of the MAPKActivators

When purified MAPK activator was incubated with [γ-$^{32}$P] ATP at high specific activity, $^{32}$P incorporation could be detected on both 46- and 45-kDa polypeptide bands correlating with the activities and protein bands of MAPK activators 1 and 2, respectively (FIG. 9). Presumably, this phosphate incorporation is due to autophosphorylation, although the rate of this reaction and its stoichiometry are very low (0.5–1 pmol/min/mg, 0.2% mol/mol).

The results presented in FIG. 9 show autophosphorylation of MAPK activators 1 and 2. The peak fractions from the last step of purification (Mono Q column), were tested for MAPK activator by the activation assay (upper panels of each) and for autophosphorylation (lower panel of each) as described under Experimental Procedure. Autophosphorylation (Materials and Methods, below; 60 min, [γ$^{32}$P]ATP- (50 cpm/fmol) was terminated by boiling with Laemmli sample buffer and proteins were separated by 12% SDS-PAGE. In FIG. 9A, the proteins were then electrophoreticaly transferred into immobilon-P which was exposed to X-ray film. In FIG. 9B, the gel was stained, destained, dryed, and exposed to the X-ray film.

In order to eliminate the possibility that the bands observed reflect contamination by MAP kinase, the autophosphorylation was repeated in presence and absence of B3. The results in FIG. 8 (above) show that the 46- and 45-kDa phosphopeptides in the MAPK activator are distinct from ERK1 and ERK2. Phosphoamino acid analysis showed that the autophosphorylation reactions led to incorporation of phosphate into serine, threonine, and tyrosine residues in the MAPK activators (FIG. 8B).

The identification of the three substrates for the MAPK activator (lysine mutant of MAP kinase, MBP, and autophosphorylation), together with the low phosphorylation of the peptide containing the TEY sequence and histones (Table 3), further corroborates the MAPKactivator as a protein kinase.

DISCUSSION OF THE FIRST SERIES OF EXAMPLES

EXAMPLES 1-5

MAPKactivators were purified as two distinct peaks (peaks 1 and 2) resolved by anion exchange chromatography of high speed supernatants of EGF-stimulated A431 cells. The extent of purification was determined to be approximately 2500-fold for both peaks from the FFQ step of purification. It was impossible to determine the MAPK activator activity in the crude cytosolic extracts, and therefore estimates of total purification are not available. However, a conservative estimate of a 5-fold purification for the first step would indicate that the MAPK activators are purified by 12,000-fold from the cytosolic extracts.

Polypeptides of 46 and 45 kDa were identified as the MAPK activators 1 and 2, respectively. This identification is supported by the following: a) the 46-kDa band directly correlated with the activity of MAPK activator 1 after the Mono Q column (FIG. 3A) and also after the Sephacryl S300 and Mono S columns (data not shown); the 45-kDa polypeptide band was elevated in the peak of activity of MAPK activator 2 (FIG. 3B), although the correlation was not perfect in this case; b) the molecular mass of the MAPK activators was shown to be between 40 and 52 kDa by SDS-PAGE, sucrose gradient centrifugation, and gel filtration, and the calculated molecular weights based on Stoke's radii and sedimentation coefficient were 47,200 and 44,500, which are close to the molecular weight of the stained bands obtained by SDS-PAGE; c) the high degree of purification (discussed above) correlated with enrichment of the 46-kDa band of MAPKactivator 1 (FIG. 4); d) the bands obtained after seven distinct purification steps in both cases represented the majority of the protein content in the peak fractions (70–90% in different preparations); and e) we observed that the MAPK activator is a protein kinase, and an autophosphorylated protein comigrated with the peak of MAPK activator activity and with the 46- and 45-kDa polypeptide bands on SDS-PAGE (FIG. 9). Along with this evidence, it was also shown that the 46-kDa band was the only phosphorylated band when this purification was performed using in vivo $^{32}$P labeling of A431 cells. Since the MAPKactivator was shown to be activated by phosphorylation (20), these results together with the data discussed above strongly suggest that the protein bands detected at molecular masses of 46 and 45 kDa with SDS-PAGE are indeed the MAPK activators.

The relationship between the two distinct MAPK activators from peaks 1 and 2 is not clear from these Examples, however, additional results presented in Examples 6–11, below, suggest that the two peaks are alternatively spliced products of the same gene. The MAPK activators from the two peaks behave differently on several chromatographic steps (FIGS. 2A, 2H, and 2I, FIGS. 3A and 3B, and FIG. 5) and slightly differ in their substrate specificity (Table 3). Therefore, the results presented in Examples 1–5, above, support the concept that the two peaks represent distinct isozymes, similar conceptually to the isozymes known for other protein kinases such as the ERK family (10). It is possible, however, from the foregoing results that only one MAPK activator exists and some form of modification is responsible for the two distinct proteins seen with chromatography, electrophoresis and sucrose density gradients. Thus, clarification of this question required cloning of the cDNAs encoding the two different forms of the MAPKK enzyme (see Examples 6–11, below).

One of the interesting questions regarding the MAPK activator is the mechanism by which it activates the MAP kinase. In previous reports several possible mechanisms were suggested, and among them the possibility that the MAPK activator does not necessarily have to be a protein kinase, but could simply stimulate MAPK autophosphorylation (19,22). The latter possibility is now considered unlikely in view of the results presented in the Examples, above, wherein the MAPK activators were shown to cause phosphate incorporation into catalytically inactive mutants of the Xenopus MAPK (FIG. 7). Thus, the present results indicate for the first time that the MAPK activators 1 and 2 are indeed protein kinases, and the inventors consider it unlikely that the observed phosphate incorporation is due to enhanced autophosphorylation, particularly since autophosphorylation of the K57R mutant was not observed (i.e., even after 18 h of incubation with $Mg^{2+}$ and ATP; data not shown). The observation that the MAPK activators are protein kinases, (hereinafter termed MAPK kinase, MAPKK), is additionally supported by: a) the existence of an independent low-level autophosphorylation activity (FIGS. 8 and 9; and, low levels of phosphorylation of several substrates seen in Table 3); and, b) phosphorylation of MBP (FIG. 8) that was closely correlated with the peak of MAPKK activity through the last three purification steps of the MAPKK purification.

Several possibilities were raised in the previous reports (19,22) regarding its possible mechanism of MAPK activation, including the concept that the MAPK activator might be a kinase, or mixture of kinases, that can either phosphorylate both threonine and tyrosine residues or phosphorylate only one of the two types of residues followed by autophosphorylation of the other. The results in the Examples, above, demonstrate that the MAPKK is probably not a mixture of protein kinases (FIGS. 3 and 4), but rather a single kinase capable of phosphorylating both threonine and tyrosine residues, particularly evident in the observed phosphorylation of the mutant Xenopus MAPK (FIG. 7). Therefore, the MAPKK seem to belong to a novel group of dual specificity protein kinases (33–36); and, with an apparent high degree of substrate specificity (i.e., MAPKK failed to efficiently phosphorylate a variety of common kinase substrates including the peptide containing the phosphorylation sites of the MAPK and the denatured MAP kinase, Table 3, and Citation 19. The latter specificity, is quite different from the behavior of other protein kinases that recognize a certain sequence of amino acids and are able to phosphorylate many target proteins or artificial peptides (39).

MATERIALS AND METHODS: FIRST SERIES OF EXAMPLES

Materials

Buffers:

Buffer H (homogenization buffer): 50 mM β-glycerophosphate, pH 7.3, 1.5 mM EGTA, 1 mM EDTA, 1 mM dithiothreitol (DTT), 0.1 mM sodium vanadate, 1 mM benzamidine, 10 μg/ml aprotinin, 10 μg/ml leupeptin, and 2 μg/ml pepstatin-A. Buffer A: 50 mM β-glycerophosphate, pH 7.3, 1.5 mM EGTA, 1 mM EDTA, 1 mM DTT, 0.1 mM sodium vanadate, and 0.01% Triton X-100 (Pierce). Buffer C: 40 mM Hepes pH 7.2, 2 mM EGTA, 1 mM EDTA 1 mM DTT and 0.01% Triton X-100. Buffer E: Buffer A without Triton X-100. Buffer R: (final reaction mixture conditions): 10 mM $MgCl_2$, 1.0 mM DTT, 50 mM β-glycerophosphate, pH 7.3, 85 mM sodium vanadate, 2 mM PKI peptide, 1.5 mM EGTA, 10 mM calmidazolium.

Columns and resins:

Mono Q HR 5/5, Mono S HR 5/5, and Superose 12 HR 10/30 FPLC columns were purchased from Pharmacia LKB. Q Sepharose—fast flow (FFQ, Pharmacia LKB) was packed either in a 5/20 HR FPLC column or in a 25/800 mm (400 ml) column for the purification. Heparin agarose (Sigma) was packed in a 25/360 mm column (180 ml). Hydroxylapatite (Calbiochem, capacity of 36 mg protein per gram resin) was mixed 2:1 with fibrous cellulose (Whatman) and packed in a 16/100 HR FPLC column. ATP agarose ( Sigma, linked through C-8) was packed in a 5/20 HR FPLC column. Sephacryl S-300 (Pharmacia LKB) was packed in a 160 ml 10/2000 mm column.

Proteins and Peptides:

ERK1 was purified from insulin stimulated Rat 1 HIRcB cells up to the DEAE-cellulose step as described by Boulton et al. (9). This preparation contained a minor amount (~10%) of ERK2. Recombinant ERK2 expressed in E. Coli was prepared as described by Boulton et al. (10), and made available to this laboratory by Regeneron Pharmaceuticals Inc. for evaluation. The following peptides were prepared by the peptide synthesis facility of the Howard Hughes Medical Institute, Seattle, Wash.: PKI peptide, TTYADFIASGRT-GRRNAIHD; ETE, RRREEETEEE; RR-SRC peptide, RRLIEDAEYAARG; TEY peptide, PEHDHTGFLTEY-VATRWYR; Syntide-2, PLARTLSVAGLPGKK; and S6 peptide, RRLSSLRA. Kemptide was from Sigma, and Band-3 peptide, MEELQDDYEDDMEERR was a gift. Epidermal growth factor (EGF, receptor grade) was purchased from UBI and dissolved in 0.5% bovine serum albumin (BSA). Casein, protamine, histones, BSA, poly ($Glu^{80}$-$Tyr^{20}$) and enolase were from Sigma, 40-S ribosomes (S6 protein) and p70 S6 kinase purified from skeletal muscles were synthesized in the inventors' laboratory, and casein kinase-II was likewise synthesized. Recombinant $pp90^{rsk}$ expressed in Baculovirus was a gift, Raf 1 was a gift, and the cAMP-dependent protein kinase catalytic subunit (cAMPdPK) was from Dr. Yuhuan Wang of this laboratory.

Methods

Preparation of cell extracts:

Human epidermal carcinoma A431 cells were grown to confluency (~$8 \times 10^7$ cells/15 cm plate) and incubated for 18 h in 0.1% fetal calf serum in Dubbelco modified Eagle medium. The cells were then treated with EGF (5 min, 100 ng/ml unless noted otherwise), the medium removed and the cells rinsed twice with ice cold phosphate buffered saline and once with ice-cold Buffer H. Cells were scraped into Buffer H (0.5 ml/plate) and disrupted by $2 \times 17$ seconds sonication (50W) followed by centrifugation at 100,000×g for 20 min at 4° C. (Beckman TLA ultracentrifuge). The resulting supernatants were then either frozen immediately at −70° C. or, where indicated, assayed immediately.

Preparation of inactive MAPK from Swiss 3T3 cells (B3):

Cytosolic extracts of quiescent Swiss 3T3 cells (clone D1) were chromatographed on a Mono Q HR 5/5 column as described (19). The fractions containing inactive forms of ERK1 and 2 were detected by assaying for their in vitro MBP kinase activity following activation with MAPKactivator from Swiss 3T3 cells (20). These fractions were pooled and stored at −70° C. We refer to the pool of inactive ERK1 and 2 as "B3" for basal peak 3 (3). Three separate preparations of B3 were used throughout this study, all of which contained comparable mounts of activatable ERKs (250 pmol/min/ml +/−15%, as judged by their activation by partially purified MAPKactivator).

Determination of MAPK activator activity:

MAPK activation assay: Aliquots (6.25 ml) of the fractions being examined were incubated with inactive MAPK (B3) or Buffer A (6.25 ml) in the presence of 100 mM [$\gamma$-$^{32}$P] ATP (1–2 cpm/fmol), and 0.83 mg/ml BSA in Buffer R (final volume of 20.8 ml) at 30° C. After 15 min, 4.2 ml of 2 mg/ml bovine myelin basic protein (MBP, Sigma) was added and the incubation was continued for another 20 min (except where indicated). Reactions were quenched by spotting 20 ml on phosphocellulose paper squares (Whatman, P81), which were washed in 150 mM phosphoric acid. Phosphate incorporation was measured using a scintillation cocktail (Ecolume, ICN). One unit of MAPK activator is defined as the amount of activator that causes a net increase in the MAPK activity of B3 as reflected by a net elevation of 1 pmol/min of MBP phosphorylation in the above reaction. The reaction described had a linear range for MAPK activator activities of up to 400 units/ml, more concentrated fractions were diluted (up to 50-fold in the final steps of purification) in Buffer C.

MAPK phosphorylation assay: Aliquots (6 ml) of the fractions being examined were incubated with 6 ml of inactive MAPK(B3) in the presence of 20 mM [$\gamma$-$^{32}$P] ATP (40–80 cpm/fmol), in Buffer R (final volume of 18 ml) at 30° C. for 10–50 min. The reaction was terminated by boiling in Laemmli sample buffer and proteins were separated by 12% polyacrylamide gel electrophoresis in the presence of sodium dodecyl sulfate (SDS-PAGE), dried, and exposed to X-ray film (XAR, Kodak). The phosphorylated MAP kinases, ERK1 and ERK2 were visualized as 44 and 42 kDa bands on the autoradiogram. Gel slices containing ERK2 were excised from the gels and phosphorylation was quantitated by scintillation counting. The MAPK activator activity is defined as the rate of phosphorylation of ERK2 in pmol/min.

Estimation of MAPKactivator activity in cytosolic extracts: MAPK activator activity could not be determined in crude extracts using either of the methods above. Accordingly, in order to estimate activity at this stage, cytosolic extracts of cell homogenates (0.5 ml) were incubated for 2 h at 4° C. with FFQ resin (0.25 ml) that had been prewashed with Buffer H. The resins were packed into small columns made from 1 ml pipet tips plugged with glass wool and washed with 4 volumes of Buffer H. Most of the MAPK activator (>80%) was retained on the column under these conditions and was then eluted from the column by addition of one column volume of 0.08M NaCl in Buffer H. MAPK activator activity was determined by MAPKactivation as described above.

Autophosphorylation: Aliquots (20 ml) of the fractions being examined were incubated in the presence of 20 mM [g-$^{32}$P] ATP (80 cpm/fmol) in Buffer R (final volume of 30 ml) at 30° C. At the indicated times the reactions were terminated with Laemmli sample buffer, separated by 12% SDS-PAGE and transferred into an Immobilon-P (Millipore) or the gels were stained, destained and dried. The membranes or dried gels were exposed to X-ray film (XAR, Kodak).

Phosphorylation of exogenous substrates: Aliquots (12.5 ml) of purified MAPK activator or Buffer C (as a control) were incubated in the presence of 20 mM [g-$^{32}$P] ATP (80 cpm/fmol) and the examined substrate in Buffer R (final volume of 25 ml) at 30° C. for 30 min. Phosphate incorporation into proteins (MBP, ERK-2, BSA, casein, protamine, ribosomal S6 protein, histones, poly (Glu$^{80}$-Tyr$^{20}$), enolase, casein kinase II, pp$^{90^{rsk}}$, p70 S6 kinase, Raf-1, and cAMPdPK), was determined by autoradiography after separation by SDS-PAGE as described above. Phosphate incorporation into peptides (Kemptide, S6 peptide, Syntide-2, RR-SKR peptide, Band 3 peptide, ETE peptide and TEY peptide) was determined by the filter paper assay, as above. Inactivation of MAPK (ERK-1) by Phosphatases:

The ERK1 preparation (0.5 ml, 4 nmol/min/ml) was desalted (by gel filtration) into a buffer containing 40 mM Hepes, pH 7.4, 2 mM EDTA, 1 mM DTT and 0.4 mg/ml BSA. The enzyme was then incubated with purified human spleen protein tyrosine phosphatase, CD45 (250 nmol/min/ml towards MBP phosphorylated on tyrosine (26)), bovine heart phosphatase-2A (100 nmol/min/ml towards phosphorylase a (3)), or both CD 45 and PP2A for 60 min at 30° C. The phosphatase reactions were terminated by addition of okadaic acid (27) and sodium vanadate, 1 µM and 2 mM, respectively.

In vitro translation and immunoprecipitation of several constructs of *Xenopus* MAP kinase:

RNA transcribed in vitro from a cDNA encoding a *Xenopus* MAPK with an amino terminal myc epitope tag or MAPK mutants were translated in a reticulocyte lysate as described (28). The $^{35}$S-labelled proteins were purified by immunoprecipitation using antibodies specific to the myc epitope, and extensively washed (28). These MAP kinases were then used as substrates for phosphorylation by MAPK activator.

Phosphoamino acid analysis:

$^{32}$P-labelled proteins were separated by SDS-PAGE and transferred to Immobilon-P membranes. Membrane slices containing the proteins were hydrolyzed in constant boiling HCl (Pierce) by the method of Kamps and Sefton (29) and analyzed by two dimensional electrophoresis (30). The $^{32}$P-labelled reticulocytelysate translated proteins were eluted from the gel and hydrolyzed in HCL (30).

Other methods:

Protein concentration was determined using Coomassie protein assay reagent (Pierce) according to Bradford (31), silver stains were according to Blum et al. (32), and electrophoretic transfer to Immobilon-P according to Burnette (33).

SECOND SERIES OF EXAMPLES

The materials and methods used in Examples 6–11 are described following Example 11, below.

EXAMPLE 6

Isolation of DNA Encoding Human MAPK Kinase Type 1a

A 46 kDa MAPKK purified from EGF stimulated A431 cells and a 45 kDa MAPKK purified from rabbit skeletal muscle (Materials and Methods, Examples 1–5, above) were used to obtain amino acid sequence for the MAPKK protein. After endoproteinase Lys-C cleavage of the A431 protein seven peptides were obtained, while trypsin or chymotrypsin digestion of the rabbit muscle enzyme provided nine peptides. Amino acid sequences that were obtained from all peptides showed that four from the rabbit muscle protein were identical to sequences obtained from the A431 protein indicating that the enzymes from both sources were similar. None of the twelve distinct peptide sequences obtained were found in the Swiss protein database. However, three of the sequences resembled consensus sequences characteristic of protein serine/threonine kinases, in particular, the yeast protein STE7, strongly suggesting that the 46 and 45 kDa polypeptides were indeed from MAPKK.

A series of degenerate oligonucleotides corresponding to the different amino acid sequences were used for PCR (Table 4, Materials and Methods, below). One main PCR product of 213 bp was amplified from cDNA prepared from EGF stimulated A431 cells (100 ng/ml, 6 hr) using degenerate oligonucleotides encoding the amino acids PTPIQLNP and the anti-coding strand for the amino acids, KISELGAG. The PCR amplification product was sequenced to confirm that it encoded part of a novel protein and was subsequently used as a probe to screen a human T-cell cDNA library. Of 26 putative clones from the initial screening of 10$^6$ plaque forming units, two distinct clones representing the entire coding sequence of MAPKK were identified.

The nucleotide and predicted amino acid sequence of a single long open reading frame of the first cDNA (MKK1a) are shown in SEQ ID NO:32 and SEQ ID NO:33; and the sequences of MKK1b are shown in SEQ ID NO:34 and SEQ ID NO:35.

SEQ ID NO:32 and SEQ ID NO:33 depict the nucleotide sequence of the MKK1a cDNA and the protein product it encodes. Nucleotide sequence was performed as described. Both coding and anti-coding strands of the clones were sequenced to give an exact match in nucleotide sequence. These nucleotide and amino acid sequences are also shown in FIG. 1 of Seger et al., J. Biol. Chem. 267:25628–25631, 1992 ("1992b"), which is incorporated by reference herein in its entirety. Therein, the proteolytic peptides obtained in amino acid sequencing are underlined and those common to both A431 cells and rabbit muscle are in bold type. Peptides 3, 9 and 11 are from the A431 cells46 kDa MAPKK and peptides 2, 5, 7, 10 and 12 are from the rabbit muscle enzyme. A * denotes a difference in the protein sequence from rabbit muscle (Q instead of K in position 104) and a ** denotes a difference in the A431 protein sequence where Q was observed instead of the DNA sequence predicted G in position 328.

SEQ ID NO:34 and SEQ ID NO:35 depict the nucleotide sequence of MKK1b cDNA and the protein product it encodes. Only a portion of MKK1b (corresponding to nucleotides 10–1280 in MKK1a, SEQ NO:32) was sequenced and found identical to the MKK1a sequence (SEQ ID NO:32) except for missing 78 nucleotides (i.e., bases 472–549 in SEQ ID NO:32). The MAPK1b coding sequence is shown in SEQ ID NO:36.

A methionine codon with flanking Kozak sequence typical of translational initiation sites (58) is located at position +34. Since it precedes the sequence PKKKPTP which was reported to be the N-terminal peptide of MAPKK from *Xenopus* (45), it is most likely that this codon represents the starting methionine. The open reading frame of MKK1a encodes a 393-residue polypeptide with molecular size of 43,439 daltons which is dose to the apparent molecular weights described above. It contains the primary sequence of the 12 peptides isolated from the A431 cells and rabbit muscle (106 amino acids) which accounts for 26% of the putative translation product. In addition, the stretch of 32 amino acids in position 186–217 is identical to that reported previously for the *Xenopus* MAPKK (45). These results, taken together with the existence of all the consensus subdomains of protein serine/threonine kinases (59), provides evidence that the cDNA shown in SEQ ID NO:32 and SEQ ID NO:34 encode MAPKK1a and MAPKK1b, respectively.

EXAMPLE 7

Expression of MAPKK in Mammalian Cells

The cDNA clone obtained in Example 6, that possessed a nucleotide sequence capable of encoding a MAPKK protein in a cell, was over-expressed in COS cells to verify that the cDNA did in fact express a legitimate MAPKK protein. To ensure optimal expression, an alanine codon (GAC) was inserted after the starting methionine of the MKK1a cDNA, i.e., providing a guanosine in position +4 of the translated mRNA (58). The modified construct was then ligated into the expression vector pCDNA1 and transfected into COS cells. Two days after transfection, the cells were harvested, lysed, examined for MAPKK protein content using anti-peptide antibodies (Materials and Methods, below) and the resultant immunoprecipitated MAPKK protein was assayed for kinase activity using an MAPK enzyme from phorbol 12-myristate 13-acetate (PMA)stimulated cells as the substrate for the kinase (19,44). Partially purified cytosolic extracts of the MKK1a-cDNA-transfected COS cells contained about 5–10-fold more MAPKK protein than mock transfected cells (see FIG. 2 in Seger et al., 1992b, supra). Moreover, when the latter transfected COS cells were stimulated with PMA (100 nM, 10 min.) MAPKK activity in cytosolic extracts was 1.5–3-fold greater than in corresponding PMA-stimulated nontransfected cells.

The results show over-expression of MKK1a in COS cells. MKK1a was modified as described under Materials and Methods, below. After 48 hours, the cells were starved for 6 hours and harvested after treatement with PMA (100 nM, 10 min) or ethanol (as a control). Activity of MAPKK was determined as described. Increase (1.5–3-fold) in MAPK activation activity after PMA-stimulation was obtained in 4 separate experiments. Proteins eluted from the DE52 columns (5 µg each lane) were analyzed by Western blotting (33) using antibodies specific for MAPKK peptide sequences (prepared as described). Increase (5–10-fold) in the amount of MAPKK was obtained in four separate experiments.

The difference between the level of activation of MAPKK enzyme activity and the level of expression of the MAPKK protein observed in these transfected COS cells may, in part, be due to improper folding of some of the recombinant protein molecules or, alternatively, to lack of sufficient upstream regulatory activators that normally stimulate the MKK within the a mitogen-treated cell. Taken together, the results in Example 6 and 7 (above) indicate that the over-expressed protein in transfected COS cells has the correct primary and secondary structure, i.e., because enzyme activity is manifest.

EXAMPLE 8

Isolation of DNA Encoding Human MAPK Kinase Type 1b

The coding region of the second clone obtained (MKK1b) was isolated and sequenced and found to have a nucleotide sequence identical to that of MKK1a (Example 6) except for a gap of 78 nucleotides (26 amino acids) in position 471–548 of SEQ ID NO:32. The single long open reading frame of MKK1b encodes a 367 residue polypeptide with a calculated molecular size of 40,714 Da. To verify that the MKK1b sequence was expressed as mRNA in a normal population of cells, mRNA was prepared from A431 cells, PCR was performed using oligonucleotides encoding the peptide AIRNQI and the anti-coding strand for the amino acids, PPKLPS. (See Table 1, above). Two amplified products were obtained (data not shown): a major one of about 600 bp as expected for MKK1a and a second one of about 500 bp as expected for MKK1b. This result, together with the fact that the predicted sequence of the MKK1b clone contained the sequences of 10 of the peptides obtained by protein sequencing plus all of the conserved kinase domains strongly suggests that at least two forms of the enzyme (i.e., type 1a and type 1b) exist in a mammalian cell; possibly representing 46 kDa and 45 kDa forms in A431 cells. The absolute identity in nucleotide sequence of type 1a and type 1b MKK1 within the common region of the two cDNA molecules makes it likely that both forms are derived from a single gene product, and that the different protein products observed are the results of alternative splicing of mRNA (e.g., similar to splicing differences described with other protein kinases, 27).

EXAMPLE 9

Oligonucleotide Probes, In Situ Hybridization, and Patterns of Expression of MAPKK in Human Tissues A probe was prepared from the N-terminal portion of the cDNA encoding MAPKK1a identified one main 2.6 kb transcript by Northern blot analysis (FIG. 12).

The results presented in FIG. 3 of Seger et al. (1992b) graphically depicts the levels of expression of MKK1 transcripts in human tissues and EGF stimulated A431 cells. An N-terminal fragment (bp 1–516), cleaved from the MKK1a clone was used as a probe in this analysis. Human Poly(A) selected RNA from A431 cells and from spleen were prepared as described before. All other human Poly(A) selected RNAs were purchased from Clontech. Northern blotting, $^{32}$P-labeling of the probe, and hybridization were performed as described below (i.e., in the Materials, Methods and Procedures). Equivalent amounts of each mRNA (2.5 µg) were used for the analysis. Methylene blue staining of the nylon membrane after the transfer showed similar amounts of KNA ranging from 0.8 to 7.0 kb in size.

Because of the small differences in size between MKK1a and MKK1b, it is likely that mRNAs encoding both type 1a and type 1b are distinguished by this in situ hybridization technique. The MKK1 transcript was detectable in all human tissues and cell lines examined. Expression levels were elevated in EGF-stimulated A431 cells and in skeletal muscle.

EXAMPLE 10

Human MAPKK Type 2 Encoded by 5.5 kb mRNA

To our surprise, although the level of MAPKK enzyme activity in the nervous system and in mitogen-stimulated cells is relatively high (21), the amount of MKK1 transcript in human brain was relatively low. However, when autoradiograms of brain mRNA Northern blots were prepared after longer exposure times a very faint band was observed at approximately 5.5 kb. The 5.5 kb form of MKK2 RNA was found in brain, but also in liver and skeletal muscle (not shown). It is considered likely by the inventors that the latter tissues contain a MKK2 transcript which encodes a distinct MAPKK2 protein. Because of the variety of organisms and cell types in which the MAPKK signaling cascade is operative, existence of more than one MAPKK may provide tissue-specific and/or growth factor-specific signaling specificity.

EXAMPLE 11

Structural and Functional Domains Within the MAPKK1 Protein

Based on genetic and biochemical data obtain from yeast (61), it was previously suggested that MAPKK1 might belong to the STE7/BYRI family of yeast protein kinases. Furthermore, partial protein sequence of MAPKK from Xenopus reportedly showed a similarity between the sequence of some of the peptides and those of the yeast kinases (45). In fact, now that the sequence of MAPKK1 is known (Examples 1 and 3), a comparison with other protein kinases shows sequence similarity with members of the STE7 family of kinases, (e.g. STE7, BYRI, WIS I and PBS2). MAPKK1a was most similar to this latter group of kinase (see FIG. 4 in Seger et al., 1992b, supra), despite the fact that the overall percent identities were lower for this group of kinases than the identities observed with other mammalian kinases and their yeast counterparts (i.e., 50–65% identify of MAPKK1a with the kinases of citation 22, 30). Interestingly, a region of 90 amino acids located in the region between subdomains "VI" and "X" appears to be highly conserved in the MAPKK family of protein kinases, displaying about 60% identity. This is significantly higher than the identity found for this region in all other protein kinases. It is therefore thought highly likely that the region between subdomains "VI" and "X" is responsible for the specificity and regulation of the MAPKK1 protein. Comparison of the amino acid sequence of MAPKK (and its yeast homologue kinases), with the kinase domains of all other protein kinases showed much lower levels of sequence identity and the scores do not predict any close relationships of MAPKK1 with these other kinases.

Although MAPKK1 was clearly shown to be a dual specificity kinase, no significant overall similarity to any of the other known dual specificity kinases (63) was obtained in a computer search. However, comparison of subdomain "XI" of MAPKK1 to those of ERK1, ERK2, SPK1, ESKI, MCK1, WEE1, STY, PYT (allowing for one gap in alignment), revealed a striking similarity of >60% (data not shown). As previously suggested (22), it is possible that homology in the latter "XI" subdomain may be related to the general specificity of protein kinase enzymes for tyrosine residues, as well as serine/threonine residues.

An additional interesting feature of the MAPKK1 sequence is the clusters of proline residues that are located within its N- and C-terminal regions of the polypeptide (i.e., amino acid residues at positions 2, 6, 8, 13, 15 and 384 and 387; SEQ ID NO:33). The exact function of these proline clusters is unclear at present, but it is possible that they serve as target sites in the MAPKK molecules for proline-directed protein kinases (12) that phosphorylate nearby serine/threonine residues. Such putative phosphorylation site sequences in MAPKK1a are the sequences "RPRTP" (i.e., at amino acid position 289–293; SEQ ID NO:33), "PSTPT" (position 384–388; SEQ ID NO:33), and "PKKKPTP" (position 2–8; SEQ ID NO:33). It has previously been suggested (61) in yeast studies that during stimulation of cells with mating factor the STE7 kinase from S. cerevisiae may be hyper-phosphorylated but not activated by FUS3. If FUS3 is a yeast counterpart of MAPK, it is possible that the MAPK enzyme in mammalian cells might participate in regulation of its own upstream transcription activator regulatory protein (i.e., MAPKK phosphorylates of its own genetic regulator). The physiological function of such phosphorylation is not entirely clear, but an interesting possibility is that it could result in a rapid inactivation of MAPKK. Such a negative regulatory mechanism could provide a means for rapidly downregulating expression of MAPK kinase activity in cells at the transcription level, e.g., down-regulation of kinase transcription such as has been observed to occur within 7–15 min after growth factor stimulation of cells (44). Thus, it is likely that alterations such as chemical modification of amino acid residues within the proline cluster regions of MAPKK, may result in enzymes with altered responsiveness to negative regulatory feedback control; and similarly, recombinant cells containing MAPKK cDNA with nucleotide replacements (i.e., substitutions) within the proline cluster regions, may result in cells having altered responsiveness to negative regulatory feedback controls.

It is also possible that one or more upstream activator proteins of MAPKK may exist that act as negative and positive regulatory elements similar to regulatory elements disclosed in yeast, e.g., upstream yeast activators of the STE7 family, (STEI 1, BYR2 and BCKI, ref. 61). In the latter case, Raf-1, a recently disclosed putative activator of MAPKK (64, 65), does not show sequence homology with the latter yeast regulatory elements, and it is possible, therefore, that additional MAPKK regulatory proteins have yet to be identified. It is considered highly likely that MAPKK negative/positive upstream regulatory elements will be identified by screening mammalian cDNAs under non-stringent conditions with degenerate probes designed for nucleotide sequence complementarity to regions of deduced amino sequences encoded by cDNAs that encode members of the STE 11 family of yeast protein kinases.

MATERIALS AND METHODS FOR EXAMPLES 6–11

Protein purification and sequencing.

A 46 kDa MAPKK1a was purified from A431 cells as previously described (44). A 45 kDa MAPKK1 was purified from rabbit muscle by a modification of the previously described in Examples 1–5, above. The proteins were then resolved by SDS-polyacrylamide gel electrophoresis, blotted onto a nitrocellulose membrane (33) and digested according to Abersold et al. (51). After Endoproteinase Lys-C cleavage (52) of the A431 protein (21 µg) and trypsin or chymotrypsin (51) digestion of the rabbit muscle enzyme (30 µg) the products were resolved on a C-8 high pressure liquid chromatogaphy column (Pierce) and sequenced using a 470A gas phase protein sequencer (Applied Biosystem).
RNA isolation.

Total RNA was extracted from human spleen and A431 cells as described (53). Total KNA was poly(A)-selected using Fast TrackTm mRNA isolation kit (Invitrogen inc.) and protocol based on established methods (54). Human Poly(A)selected RNAs from thymus, brain, kidney, skeletal muscle, heart, lung, and small intestine were purchased from Clontech Laboratories Inc.
Amplification of a partial cDNA encoding the MAPKK.

Degenerate sense and antisense oligonucleotides (23 bases) corresponding to the amino acid sequences PTPIQLNP and KISELGAG, respectively, were synthesized by the chemical synthesis facility, Howard Hughes Medical Institute, Seattle, Wash. First strand cDNA was synthesized as previously described (55) using poly (A)-selected RNA isolated from EGF-stimulated (100 ng, 6 hr) A431 cells. Polymerase chain reaction (PCR) was corded out in a reaction mixture (50 μl) containing: 10 mM Tris-HCl, pH 8.8, 50 mM KCl, 1.5 mM MgCl$_2$, dATP, dGTP, dCTP, and dTTP (0.2 mM each), 0.1% Triton X-100, 1.5% dimethyl sulfoxide, 20 ng first strand cDNA, 1 μM sense oligomer, 1 μM antisense oligomer, and 5 units of Taq DNA polymerase (Promega). Reaction conditions were: 94° C. for 1 min. followed by 48° C. for 1.5 min and then, 72° C. for 2 min for 30 cycles (Hybaid thermal reactor, National Labnet Ltd). The resulting DNA products were analyzed on a 1% agarose gel and ligated into the PCRII vector (Invitrogen Inc.) as recommended by the manufacturer.

Human T-Cell cDNA library screening and DNA sequencing.

Approximately 10$^6$ plaque forming units were screened as described previously (55) using the $^{32}$P-labeled 213 bp partial cDNA obtained by PCR using the primers shown in Table 4, below.

first 55 bp of the clone using PCK (55). The product was then ligated into EcoRl and BamHl digested pCDNA I vector DNA (Invitrogen Inc.), propagated in XL-1 cells (56) and sequenced to ensure its correct composition. Plasmid DNA was prepared using an adaptation of the alkaline lysis method (55) and purified using Qiagen Tip-500 columns as recommended by the manufacturer. COS-7 cells were transfected with the construct using Gene Pulse™ (Bio-Rad) and cultured in Dulbecco's modified Eagle's Medium (Sigma) supplemented with 10% fetal calf serum for 48 hr.

MAPKK1 detection.

MAPKK enzyme activity and total protein concentration were determined as previously described (see Materials and Methods, Examples 1–5, above) except that DE52 (Pharmacia) was used instead of QSepharose. Anti-peptide antibodies were used to detect the MAPKK1 in the DE52 flowthrough. These antibodies were raised (57) against SEQ. ID. NO. 13 listed in Table 5, below.

TABLE 4

Degenerate PCR Primers used in cDNA Cloning of MKK1

| # | Nucleotide Sequence | # | Nucleotide Sequence |
|---|---|---|---|
| 56S | AAGATAGAAGAACTAGGAGCAGA<br>    A   C   G    GT  G   G      G<br>    T            C  C  C<br>                T  T  T | 59A | TTTTGAGTTATTTCAAGGTGTAT<br>    C   G    G   C    G    A   G<br>            C   A     C      A<br>            T         T |
| 56A | TCAGCACCAAGTTCTTCTATCTT<br>    G   G   G AC  C    G   T<br>    C   C   C      A<br>    T   T   T | 57S | CCAACACCAATACAGCTAAACCC<br>    G   G   G   C   AT G   T<br>    C   C   C   T      C<br>    T   T   T      T |
| 59S | ATACACCTAGAAATAACACAAAA<br>    C   T   G   C   G   G<br>    T      C       T   C<br>    T           T | 57A | GGGTTAAGCTGGATAGGAGTAGG<br>    A   G AT  T   G   G   G<br>    C      A   C   C   C<br>                T  T  T |

(Note that: cloning using the Table 4 degenerate primers derived from amino acid sequence data was somewhat problematic because the sequences were not specific for MKK cDNA, i.e., cDNAs for other gene products were obtained. As described in the Examples 6–7, above, anti-peptide antibodies and expression in COS cells were used for final identification of MKK cDNAs. The sequence of MKK (i.e., shown in SEQ ID NO:32 and SEQ ID NO:34) now provides a variety of useful probes for cloning MKK cDNAs and genomic DNA, e.g., see Table 1, Detailed Description of the Invention, above.)

The cDNA obtained from PCR was radiolabeled using α-$^{32}$P-dCTP (NEN) as previously described (55). Putative clones were plaque purified and subcloned (55) into pBluescript SK(–) vector (Stratagene Cloning Systems). Sequencing was performed using the dideoxynucleotide chain termination method (52). Synthetic oligonucleotides (chemical synthesis facility, Howard Hughes Medical Institute, Seattle, Wash.) complementary to the insert cDNA or flanking plasmid sequences were used to prime the template to attain overlapping sequences. Sequencing ladders were generated using α-$^{35}$S-dATP (Amersham) and either Sequenase® (United States Biochemical) or TaqTrack® (Promega) sequencing kits. All sequence was verified by sequencing both strands of the DNA.

COS Cell Transfections.

The MKK1a cDNA was modified by including the oligonucleotide, GGATCCGCCGCCACCATGGCAC-CCAAGAAGAAGCCG (SEQ ID NO:25), instead of the

TABLE 5

| MAPKK1 Specific Antibodies | | |
|---|---|---|
| Antibody # | Antigen: Amino Acid sequence | SEQ. ID. NO. |
| 1 | CKKPTPIQLNPS | 13 |
| 2 | CKLIHLEITQ | 14 |
| 3 | CSTIGLAGPSTPTHAAGV | 15 |
| 4 | SVLGLIGEPIRGAKKC | 16 |

The peptide antigens identified in Table 5 were synthesized by the chemical synthesis facility, Howard Hughes Medical Institute, Seattle, Wash. Peptide CKKPTPIQLNPS was modified from residues 4–13 of the MAPKK1a sequence.

Northern Analyses.

Northern analyses were carried out using established methods described previously (55). In brief 2.5 μg of poly (A)-selected RNA was electrophoresed on a 1.2% agarose/6.7% formaldehyde gel. The RNA was transferred by capillary elution to a nylon membrane (HybondTm-N, Amersham) with 20× SSC. The RNA was fixed to the membrane using a BIOSLINK™ 254T UV-crosslinking apparatus. The blots were stained with methylene blue to confirm the uniform transfer of RNA and incubated in hybridization buffer (50% formamide, 1× SSC, 25 mM Na-PO$_4$ (pH=7.0), 2× Denhardt's solution, 1 0% dextran sulfate, and 0.1 mg/ml Salmon sperm DNA) at 43° C. for 1 hr. Heat-denatured DNA probes were added to the hybridization solution ($10^6$ cpm/ml) and incubated 12 hr at 43° C. The blots were washed three times with 2× SSC/0.1% SDS for 15 minutes at 23° C., and twice with 0.1× SSC/0.1% SDS for 20 min at 43° C. The blots were exposed to X-ray film at −70° C. for 72 hr.

THIRD SERIES OF EXAMPLES

EXAMPLE 12

Bacterial Expression Systems: MAPKK

For analysis of agents that modulate the activity of MAPKK, it was necessary to produce sufficient protein for biochemical assays. For this purpose MKK1 was inserted into the bacterial expression vector pQE-9 and introduced into E. coli. The resultant transformed bacterial cells synthesize MAPKK1a protein. The recombinant MAPKK1a protein was purified from bacterial extracts using a nickle-Sepharose column. Purified product migrated as two main band on 12% SDS-PAGE. The upper band is most likely the intact full length protein with apparent molecular weight of 45 kDa. The lower band (apparent MW 39 kDa) is probably a degradation product. The identity of the MAPKK1a was confirmed by immunoblots using the anti-MAPKK antibodies (Table 4, above). As expected, because of the lack of an upstream activator, the recombinant MAPKK failed to phosphorylate MAPK, however, this protein is suitable for use as a substrate for MAPK, (and probably other MAPKK activators), in assays similar to those used in the Examples above with purified A431 MAPKK. The bacterial MAPKK1a is also probably useful as an antigen in developing monoclonal antibodies specific for MAPKK1a, and epitopes within the protein.

EXAMPLE 13

Cloning of MAPKK1 Genomic DNA

The MKK1a cDNA isolated in Example 6, above, was used to probe a genomic cosmid human T-cell library for genomic DNA encoding MAPKK1 mRNA. A clone containing a 14 kb genomic DNA insert was identified by stringent hybridization with a labeled MKK1a DNA probe (i.e., containing residues 1–512 of the sequence in SEQ ID NO:32; as described in Example 6, above).

Citations

1. Ray, L. B., and Sturgill, T. W. (1987) *Proc. Natl. Acad. Sci. U.S.A.* 84, 1502–1506.
2. Ray, L. B., and Sturgill, T. W. (1988) *J. Biol. Chem.* 263, 12721–12727
3. Ahn, N. G., Weiel, J. E., Chan, C. P., and Krebs, E. G. (1990) *J. Biol. Chem.* 265, 11487 11494
4. Anderson, N. G., Maller, J. L., Tonks, N. K., and Sturgill, T. W. (1990) *Nature* 143, 651–653
5. Boulton, T. G., Yancopoulos, G. D., Gregory, J. S., Slaughter, C., Moomaw, C., Hsu, J., and Cobb, M. H. (1990) *Science* 249, 64–67
6. Sturgill, T. W., and Wu, J. (1991) *Biochim. Bioshys. Acta* 1092, 350–357
7. Cobb, M. H., Boulton, T. G., and Robbins, D. J. (1992) *Cell Regut.* 2, 965–978
8. Thomas, G. (1992) *Cell* 68, 3–6
9. Boulton, T. G., Gregory, J. S., and Cobb, M. H. (1991) *Biochemistry* 30, 278–286
10. Boulton, T. G., Nye, S. H., Robbins, D. J., lp, Y. N., Radziejewska, E., Morgenbesser, S., Depinho, R., Panayotatos, N., Cobb, M. H., and Yancopoulos, G. D. (1991) *Cell* 65, 663–675
11. Pulverer, B. J., Kyriakis, J. M., Avruch, J., Nikolakaki, E., and Woodgett, J. R. (1991) *Nature* 253, 670–674
12. Alvarez, E., Northwood, I. C., Gonzales, F. A., Latour, D. A., Seth, A., Abate, C., Curran, T., and Davis, R. J. (1991) *J. Biol. Chem.* 266,15277 15285
13. Anderson, N. G., Li, P., Marsden, L. A., Williams, N., Roberts, T. M., and Sturgill, T. W. (1991) *Biochem. J.* 277, 573–576
14. Takishima, K., Griswold-Prenner, I., Ingebritsen, T., and Rosner, M. R. (1991) *Proc. Natl. Acad. Sci. U.S.A.* 88 2520–2524
15. Sturgill, T. W., Ray, L. B., Erickson, E., and Maller, J. L. (1988) *Nature* 334, 715–718
16. Gregory, J. S., Boulton, T. G., Sang, B. C., and Cobb M. H. (1989) *J. Biol. Chem.* 264, 18397–18441
17. Ahn, N. G., and Krebs, E. G. (1990) *J. Biol. Chem.* 265, 11495 11501
18. Payne, D. M., Rossomando, A. J., Martino, P., Erickson, A. K., Her, J. -H., Shabanowitz, J., Hunt, D. F., Weber, M. J., and Sturgill, T. W. (1991) *EMBO J.* 10, 885 892
19. Ahn, N. G., Seger, R., Bratlien, R. L., Diltz, C. D., Tonks N. K., and Krebs, E. G. (1991) *J. Biol. Chem.* 266, 4220–4227
20. Gomez, N., and Cohen, P. (1991) *Nature* 353, 170–173
21. Ahn, N. G., Robbins, D. J., Haycock, J. W., Seger, R., Cobb, M. H., and Krebs, E. G. (1992) *J. Neurochem.*, 59:147–156.
22. Seger, R., Ahn, N. G., Boulton, T. G., Yancopoulos, G. D., Panayotatos, N., Radziejewska, E., Ericsson, L., Bratlein, R. L., Cobb, M. H., and Krebs, E. G. (1991) *Proc. Natl. Acad. Sci. U.S.A.* 88, 6142–6146
23. Crews, C. M., Alessandrini, A. A., and Erikson, R. L. (1991) *Proc. Natl. Acad. Sci. U.S.A.* 88, 8845–8849
24. Wu, T., Rossomando, A. J., Her, J, -H., Del-Vecchio, R., Weber, M. J., and Sturgill, T. W. (1991) *Proc. Natt. Acad. Sci. U.S.A.* 88, 9508–9512
25. Robbins, D. J., and Cobb, M. H. (1992) *Mol. Biol. Cell* 3, 299–308
26. Tonks, N. K., Charbonneau, H., Diltz, C. D., Fischer, E. H., and Walsh, K. A. (1988) *Biochemistry* 27, 8695 8701
27. Cohen, P., Holmes, C. F. B., and Tsakitani, Y. (1990) *Trends Biochem. Sci.* 15, 98 102
28. Posada, J., and Cooper, J. A. (1992) *Science* 255, 212–215
29. Kamps, M. P., and Sefton, B. M. (1989) *Anal. Biochem.* 176, 22–27
30. Cooper, J. A., Seton, B. M., and Hunter, T. (1983) *Methods Enzymol.* 99,387 402
31. Bradford, M. M. (1976) *Anal. Biochem.* 72, 248–254
32. Blum, H., Beier, H., and Gross, H. J. (1987) *Electrophoresis* 8, 93–99
33. Burnette, W. N. (1981) *Anal. Biochem.* 112, 195–203
34. Dailey, D., Schieven, G. L., Lim, M. Y., Marquardt, H., Gilmore, T., Thorner, J., and Martin, G. S. (1990) *Mol. Cell. Biol.* 10, 6244–6256
35. Stern, D. F., Zheng, P., Beidler, D. R., and Zerillo, C. (1991) *Mot. Cell. Biol.* 11, 987–1001
36. Howell, B. W., Afar, D. E. H., Lew, J,, Douville, E. M. J., Icely, P. L. E., Gray, D. A., and Bell, J. C. (1991) *Mol. Cell. Biol.* 11, 568–572
37. Ben-David, Y., Litwin, K., Tannock, L., Bernstin, A., and Pawson, T.(1991) *EMBO J.* 10, 317 325
38. Sanghera, J. S., Paddon, H. B., Bader, S. A., and Pelech, S. L. (1990) *J. Biol. Chem.* 265, 52 57

39. Kennelly, P. J., and Krebs, E.G. (1991) *J. Biol. Chem.* 266, 15555–15558
40. Matsuda, S., Kosako, H., Takenaka, K., Moriyama, K., Sakai, H., Akiyama, T., Gotoh, Y., and Nishida, E. (1992) *EMBO J.* 11, 973–982
41. Pelech S. L., and Senghera, J. S. (1992) *Trends Biochem. Sci.* 17, 233–236.
42. Pelech S. L., and Senghera, J. S.(1992) *Science* 257, 1366–1367.
43. Ahn N. G., Seger R., and Krebs E. G. (1992) *Current Opinions in Cell Biol.* in press.
44. Seger, R., Ahn, N. G., Posada, J., Munar, E. S. Jensen, A. M. Cooper, J. A., Cobb, M. H. and Krebs, E. G. (1992) *J. Biol. Chem.* 267, 14373–14381.
45. Kasako, Gotoh, Y., Matsuda, S., Ishikawa, M. and Nishida, E. (1992) *EMBO J.* 11, 2923–2908.
46. Shirakabe, K., Gotoh, Y. and Nishida, E. (1992) *J. Biol. Chem.* 267, 16685–16690.
47. Nakielny, S., Cohen, P., Wu, J. and Sturgill, T. (1992) *EMBO J*. 11, 2123–2128.
48. L'Allemain, G., Her, J. H., Wu, J., Sturgill, T. W. and Weber, M. J. (1992) *J. Mol. Cell Biol* 12, 2222–2229.
49. Adams P. D. and Parker, P. J. (1992) *J. Biol. Chem.* 267, 13135–13138.
50. Rossomando, A., Wu, J., Weber, M. J. and Sturgill, T. W. (1992) *Proc. Natl. Acad. Sci. U.S.A.* 89, 5221–5225.
51. Abersold, R. H., Leavitt, J., saavedra, R. A., Hood, L. E. and Kent, B. H. (1987) *Proc. Natl. Acad. Sci. U.S.A.* 84, 6970–6974.
52. Masaki, T., Tanabe, M., Nakamura, K. and Soejeima, M. (1981) *Biochem. Bioshys. Acta* 660, 44–55.
53. Frohman, M. A., Dush, M. K. and Martin, G. R. (1988) *Proc. Natl. Acad Sci. USA* 85, 8998–9002.
54. Sonnemburg, W. K., Mullaney, P. J., and Beavo, J. A. (1991) *J. Biol. Chem.* 266, 17655–17661.
55. Sonnenburg, W. K., Seger, D. and Beavo J. A. (1992) *J. Biol. Chem.*, in press.
56. Ludvig, N., Burmaister, V., Jobe, P. C. and Kincaid, R. L, (1991) *Neuroscience* 44, 491–500.
57. Boulton, T. G. and Cobb, M. H. (1991) *Cell Regulation* 2, 357–365.
58. Kozak, M., (1991) *J. Biol. Chem.* 266, 19867–19870.
59. Hanks, S. K., Quinn, A. M. and Hunter T. (1988) *Science* 241, 42–52.
60. Reinhard, C., Thomas, G. and Kozma G. S. (1992) *Proc. Natl. Acad Sci. U.S.A.* 89, 4052–4056.
61. Zhou, Z., Gartner, A., Cade, R., Ammerer, G. and Errede, B. (1992) *EMBO J.* in press.
62. Lee, M. G. and Nurse, P. (1987) *Nature* 327, 31–33.
63. Lindberg, R. A., Quinn, A. M. and Hunter, T. (1992) *Trends Biochem. Sci.* 17, 114–119.
64. Kyriakis, J. M., App, H., Zhang, X., Banerjee, P., Brautigan, D. L., Rapp, U. R. and Avruch, J. (1992) *Nature* 358, 417–421.
65. Dent. P., Haser, W., Haystead, T. A. J., Vincent, L. A., Roberts, T. M. and Sturgill, T. W. (1992) *Science* 257, 1404–1406.
66. Higgins, D. G. and Sharp, P. M. (1988) *Gene* 73, 237–246.
67. Goslin, K. and Banker, G. (1991) *In: Culturing Nerve Cells* (Banker, G. and Goslin, K. Eds.), MIT Press, Cambridge, Mass., 251–258.

While the preferred embodiment of the invention has been illustrated and described, it will be appreciated that various changes can be made therein without departing from the spirit and scope of the invention.

---

---

The embodiments of the invention in which an exclusive property or privilege is claimed are defined as follows:

1. An isolated polynucleotide having the sequence shown in SEQ ID NO:32 or its complement and which encodes mitogen activated protein kinase kinase protein.

2. An isolated polynucleotide having the sequence shown in SEQ ID NO:34 or its complement and which encodes mitogen activated protein kinase kinase protein.

3. An isolated polynucleotide which encodes the polypeptide shown in SEQ ID NO:33.

4. An isolated polynucleotide which encodes the polypeptide shown in SEQ ID NO:35.

* * * * *

UNITED STATES PATENT AND TRADEMARK OFFICE
CERTIFICATE OF CORRECTION

PATENT NO. : 5,663,314                    Page 1 of 10
DATED      : September 2, 1997
INVENTOR(S) : R. Seger et al.

It is certified that error appears in the above-indentified patent and that said Letters Patent is hereby corrected as shown below:

On the title page,

| COLUMN | LINE | |
|---|---|---|
| [56] Pg. 1, col. 1 | Refs. Cited (Other Publs., Item 3) | "11487 11494." should read --11487-11494.-- |
| [56] Pg. 1, col. 1 | Refs. Cited (Other Publs., Item 6) | "*Bioshys.*" should read --*Biophys.*-- |
| [56] Pg. 1, col. 1 | Refs. Cited (Other Publs., Item 10) | "Y.N.," should read --Ip, N.Y.-- |
| [56] Pg. 1, col. 1 | Refs. Cited (Other Publs., Item 12) | "Northwood, 1.C.," should read --Northwood, L.C.,-- |
| [56] Pg. 1, col. 1 | Refs. Cited (Other Publs., Item 12) | "266,15277 15285." should read --266, 15277-15285.-- |
| [56] Pg. 1, col. 1 | Refs. Cited (Other Publs., Item 14) | After "88" insert --,-- |
| [56] Pg. 1, col. 2 | Refs. Cited (Other Publs., Item 17) | "11495 11501." should read --11495-11501.-- |

UNITED STATES PATENT AND TRADEMARK OFFICE
CERTIFICATE OF CORRECTION

PATENT NO. : 5,663,314
DATED : September 2, 1997
INVENTOR(S) : R. Seger et al.

It is certified that error appears in the above-indentified patent and that said Letters Patent is hereby corrected as shown below:

| COLUMN | LINE | |
|---|---|---|
| [56] Pg. 1, col. 2 | Refs. Cited (Other Publs., Item 18) | "885 892." should read --885-892.-- |
| [56] Pg. 1, col. 2 | Refs. Cited (Other Publs., Item 22) | "Panayotatos, N" should read --Panayotatos, N.,-- |
| [56] Pg. 1, col. 2 | Refs. Cited (Other Publs., Item 24) | "*Natt.*" should read --*Natl.*-- |
| [56] Pg. 1, col. 2 | Refs. Cited (Other Publs., Item 26) | "8695 8701." should read --8695-8701.-- |
| [56] Pg. 1, col. 2 | Refs. Cited (Other Publs., Item 27) | "98 102." should read --98-102.-- |
| [56] Pg. 1, col. 2 | Refs. Cited (Other Publs., Item 30) | "Jenson, A.M." should read --Jensen, A.M.,-- |
| [56] Pg. 1, col. 2 | Refs. Cited (Other Publs., Item 31) | "*EMBOJ.*" should read --*EMBO J.*-- |

UNITED STATES PATENT AND TRADEMARK OFFICE
CERTIFICATE OF CORRECTION

PATENT NO. : 5,663,314
DATED : September 2, 1997
INVENTOR(S) : R. Seger et al.

Page 3 of 10

It is certified that error appears in the above-indentified patent and that said Letters Patent is hereby corrected as shown below:

COLUMN      LINE

[56] Pg. 1, col. 2    Refs. Cited (Other Publs., Item 34)    After "2222-2229" insert --.--

[56] Pg. 1, col. 2    Refs. Cited (Other Publs., Item 35)    "Adams P.D." should read --Adams, P.D.,--

[56] Pg. 1, col. 2    Refs. Cited (Other Publs., Item 35)    "(1 992)" should read --(1992)--

[56] Pg. 2, col. 1    Refs. Cited (Other Publs., Item 40)    "(I992)" should read --(1992)--

[56] Pg. 2, col. 1    Refs. Cited (Other Publs., Item 49)    After "kinase" insert --kinases--

[56] Pg. 2, col. 2    Refs. Cited (Other Publs., Item 52)    After "Chapters 9 and 11" insert --.--

[56] Pg. 2, col. 2    Refs. Cited (Other Publs., Item 53)    "p." should read --pp.--

UNITED STATES PATENT AND TRADEMARK OFFICE
CERTIFICATE OF CORRECTION

PATENT NO. : 5,663,314
DATED : September 2, 1997
INVENTOR(S) : R. Seger et al.

Page 4 of 10

It is certified that error appears in the above-indentified patent and that said Letters Patent is hereby corrected as shown below:

| COLUMN | LINE | |
|---|---|---|
| [56] Pg. 2, col. 2 | Refs. Cited (Other Publs., Item 53) | "1988." should read --1986.-- |
| 1 | 32 | "cells)." should read --cells.-- |
| 1 | 48 | "pp90$^{rsk}$" should read --pp90$^{rsk}$-- |
| 3 | 4 | "pp90$^{rsk}$" should read --pp90$^{rsk}$-- |
| 3 | 13 | "pp90$^{rsk}$" should read --pp90$^{rsk}$-- |
| 5 | 9 | "as little a" should read --as little as-- |
| 5 | 11-12 | "trancription" should read --transcription-- |
| 5 | 18 | "vital" should read --viral-- |
| 6 | 2 | "c)the" should read --c) the-- |
| 6 | 14 | ""term signal" should read --term "signal-- |
| 6 (TABLE 1, under "Antisense") | 59 last line | "ACATGGCAAACCACCCGGG" should read --ACATGGCAAACCACCGGG-- |
| 7 | 20 | "it it" should read --it is-- |

UNITED STATES PATENT AND TRADEMARK OFFICE
CERTIFICATE OF CORRECTION

PATENT NO. : 5,663,314
DATED : September 2, 1997
INVENTOR(S) : R. Seger et al.

It is certified that error appears in the above-indentified patent and that said Letters Patent is hereby corrected as shown below:

| COLUMN | LINE | |
|---|---|---|
| 7 | 27 | "nucleic of" should read --nucleic acids of-- |
| 7 | 28 | "a cells," should read --cells,-- |
| 7 | 44 | "KNA)." should read --RNA).-- |
| 8 | 10 | "carders," should read --carriers,-- |
| 8 | 13-14 | "a immunoassay" should read --an immunoassay-- |
| 8 | 38 | "et at.," should read --et al.,-- |
| 8 | 39 | "67(20)" should read --267(20)-- |
| 8 | 40 | "et at.," should read --et al.,-- |
| 9 | 43-44 | "an fast" should read --a fast-- |
| 10 | 18 | "remits" should read --results-- |
| 10 | 39 | "Peak: 1" should read --Peak 1-- |
| 10 | 44 | After "increasing" delete "5" |
| 10 | 45 | Before "600" delete "(" |
| 10 | 53 | "fluted" should read --eluted-- |
| 11 | 49 | "2H," should read --2H),-- |

UNITED STATES PATENT AND TRADEMARK OFFICE
CERTIFICATE OF CORRECTION

PATENT NO. : 5,663,314
DATED : September 2, 1997
INVENTOR(S) : R. Seger et al.

Page 6 of 10

It is certified that error appears in the above-indentified patent and that said Letters Patent is hereby corrected as shown below:

| COLUMN | LINE | |
|---|---|---|
| 12 | 3 | "and2" should read --and 2-- |
| 13 (TABLE 2, under "Peak 1") | 20 line 5 | "Sepharcryl" should read --Sephacryl-- |
| 13 (TABLE 2, under "Peak 2") | 27 line 5 | "Sepharcryl" should read --Sephacryl-- |
| 13 | 61 | "mount" should read --amount-- |
| 15 | 8 | "mount" should read --amount-- |
| 15 | 35 | "45ul" should read --45µl-- |
| 15 | 38 | "closed triangle ∆," should read --closed triangle ▲,-- |
| 15 | 52 | "Buffer K" should read --Buffer R-- |
| 16 | 17 | "(TI88V)," should read --(T188V),-- |
| 16 | 18 | "(YI90F)," should read --(Y190F),-- |
| 16 | 61 | "sting," should read --staining,-- |

UNITED STATES PATENT AND TRADEMARK OFFICE
CERTIFICATE OF CORRECTION

PATENT NO. : 5,663,314
DATED : September 2, 1997
INVENTOR(S) : R. Seger et al.

It is certified that error appears in the above-indentified patent and that said Letters Patent is hereby corrected as shown below:

| COLUMN | LINE | |
|---|---|---|
| 17 (TABLE 3, under "Substrate") | 48 line 4 | "(1 Mm)" should read --(1 mM)-- |
| 17 (TABLE 3, under "Substrate") | 54 line 11 | "(20 μg/ml)" should not be superscripted |
| 17 (TABLE 3, under "Substrate") | 55 line 12 | "ζS6" should read --p70 S6-- |
| 17 (TABLE 3, under "Substrate") | 62 line 20 | "Bank" should read --Band-- |
| 18 (TABLE 3, of footnote | 9 line 1 "c") | "50 ul" should read --50 μl-- |
| 18 | 33 | "8B, The" should read --8B, the-- |
| 20 | 55 | After "specificity" delete "," |
| 21 | 6 | After "EDTA" insert --,-- |
| 21 | 46 | "pp90$^{rsk}$" should read --pp90$^{rsk}$-- |

UNITED STATES PATENT AND TRADEMARK OFFICE
CERTIFICATE OF CORRECTION

PATENT NO. : 5,663,314
DATED : September 2, 1997
INVENTOR(S) : R. Seger et al.

It is certified that error appears in the above-indentified patent and that said Letters Patent is hereby corrected as shown below:

| COLUMN | LINE | |
|---|---|---|
| 22 | 8 | "mounts" should read --amounts-- |
| 23 | 8 | "$pp90^{rsk}$," should read --$pp90^{rsk}$,-- |
| 23 | 12 | "RR-SKR" should read --RR-SRC-- |
| 23 | 22 | "a" should be underlined |
| 24 | 39 | "cells46" should read --cells 46-- |
| 24 | 49 | "SEQ NO:32)" should read --SEQ ID NO:32)-- |
| 24 | 61 | "dose" should read --close-- |
| 25 | 37 | "treatement" should read --treatment-- |
| 26 | 47 | "KNA" should read --RNA-- |
| 27 | 12 | "obtain" should read --obtained-- |
| 27 | 41 | "dearly" should read --clearly-- |
| 28 | 52 | "chromatogaphy" should read --chromatography-- |
| 28 | 56 | "KNA" should read --RNA-- |
| 29 | 3 | "corded" should read --conied-- |
| 29 | 4 | "Tris-HCl," should read --Tris-HCI,-- |

UNITED STATES PATENT AND TRADEMARK OFFICE
CERTIFICATE OF CORRECTION

PATENT NO. : 5,663,314  
DATED : September 2, 1997  
INVENTOR(S) : R. Seger et al.

Page 9 of 10

It is certified that error appears in the above-indentified patent and that said Letters Patent is hereby corrected as shown below:

| COLUMN | LINE | |
|---|---|---|
| 30 | 1 | "PCK" should read --PCR-- |
| 31 | 55 | "11487 11494" should read --11487-11494-- |
| 31 | 61 | "*Bioshys.*" should read --*Biophys.*-- |
| 32 | 9 | "15277 15285" should read --15277-15285-- |
| 32 | 20 | "11495 11501" should read --11495-11501-- |
| 32 | 23 | "885 892" should read --885-892-- |
| 32 | 37 | "Her, J,-H.," should read --Her, J.-H.,-- |
| 32 | 38 | "*Natt.*" should read --*Natl.*-- |
| 32 | 43 | "8695 8701" should read --8695-8701-- |
| 32 | 45 | "98 102" should read --98-102-- |
| 32 | 51 | "387 402" should read --387-402-- |
| 32 | 60 | "*Mot.*" should read --*Mol.*-- |
| 32 | 65 | "317 325" should read --317-325-- |
| 32 | 67 | "52 57" should read --52-57-- |

UNITED STATES PATENT AND TRADEMARK OFFICE
CERTIFICATE OF CORRECTION

PATENT NO. : 5,663,314
DATED : September 2, 1997
INVENTOR(S) : R. Seger et al.

It is certified that error appears in the above-indentified patent and that said Letters Patent is hereby corrected as shown below:

| COLUMN | LINE | |
|---|---|---|
| 33 | 16 | "2923-2908" should read --2903-2908-- |
| 33 | 31 | "*Bioshys.*" should read --*Biophys.*-- |

Signed and Sealed this

First Day of June, 1999

Attest:

Attesting Officer

Q. TODD DICKINSON

*Acting Commissioner of Patents and Trademarks*

SEQUENCE LISTING ( 1 ) GENERAL INFORMATION:

( i i i ) NUMBER OF SEQUENCES:36

( 2 ) INFORMATION FOR SEQ ID NO:1:

( i ) SEQUENCE CHARACTERISTICS:
        ( A ) LENGTH:18 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:Probe/PCR primer for MAPKK ( i x ) SEQUENCE DESCRIPTION: SEQ ID NO:1:

ACGCCTATTC AGTTGAAC 18

( 2 ) INFORMATION FOR SEQ ID NO:2:

( i ) SEQUENCE CHARACTERISTICS:
        ( A ) LENGTH:18 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:Probe/PCR primer for MAPKK ( i x ) SEQUENCE DESCRIPTION: SEQ ID NO:2:

GATGACGACT TTGAGAAG 18

( 2 ) INFORMATION FOR SEQ ID NO:3:

( i ) SEQUENCE CHARACTERISTICS:
        ( A ) LENGTH:18 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:Probe/PCR primer for MAPKK ( i x ) SEQUENCE DESCRIPTION: SEQ ID NO:3:

CAATCCGGAA CCAGATCA 18

( 2 ) INFORMATION FOR SEQ ID NO:4:

( i ) SEQUENCE CHARACTERISTICS:
        ( A ) LENGTH:18 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:Probe/PCR primer for MAPKK ( i x ) SEQUENCE DESCRIPTION: SEQ ID NO:4:

GTCAGCGGGC AGCTCATC 18

( 2 ) INFORMATION FOR SEQ ID NO:5:

( i ) SEQUENCE CHARACTERISTICS:
        ( A ) LENGTH:18 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:Probe/PCR primer for MAPKK ( i x ) SEQUENCE DESCRIPTION: SEQ ID NO:5:

CGACCTCCCA TGGCAATT 18

( 2 ) INFORMATION FOR SEQ ID NO:6:

( i ) SEQUENCE CHARACTERISTICS:
        ( A ) LENGTH:18 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:Probe/PCR primer for MAPKK ( i x ) SEQUENCE DESCRIPTION: SEQ ID NO:6:

CCCGGTGGTT TGCCATGT 18

( 2 ) INFORMATION FOR SEQ ID NO:7:

( i ) SEQUENCE CHARACTERISTICS:
        ( A ) LENGTH:18 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:Probe/PCR primer for MAPKK ( i x ) SEQUENCE DESCRIPTION: SEQ ID NO:7:

TGGTCCCGTT AACTGCAG 18

( 2 ) INFORMATION FOR SEQ ID NO:8:

( i ) SEQUENCE CHARACTERISTICS:
        ( A ) LENGTH:18 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:Probe/PCR primer for MAPKK ( i x ) SEQUENCE DESCRIPTION: SEQ ID NO:8:

GCCAGAAGGC TTGTGGGA 18

( 2 ) INFORMATION FOR SEQ ID NO:9:

( i ) SEQUENCE CHARACTERISTICS:
        ( A ) LENGTH:17 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:Probe/PCR primer for MAPKK ( i x ) SEQUENCE DESCRIPTION: SEQ ID NO:9:

AGCCCACGAT GTACGGA 17

( 2 ) INFORMATION FOR SEQ ID NO:10:

( i ) SEQUENCE CHARACTERISTICS:
        ( A ) LENGTH:18 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:Probe/PCR primer for MAPKK ( i x ) SEQUENCE DESCRIPTION: SEQ ID NO:10:

GATGAGCTGC CCGCTGAC 18

( 2 ) INFORMATION FOR SEQ ID NO:11:

( i ) SEQUENCE CHARACTERISTICS:
        ( A ) LENGTH:18 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:Probe/PCR primer for MAPKK ( i x ) SEQUENCE DESCRIPTION: SEQ ID NO:11:

AATTGCCATG GGAGGTCG 18

( 2 ) INFORMATION FOR SEQ ID NO:12:

( i ) SEQUENCE CHARACTERISTICS:
        ( A ) LENGTH:18 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:Probe/PCR primer for MAPKK ( i x ) SEQUENCE DESCRIPTION: SEQ ID NO:12:

ACATGGCAAA CCACCGGG 18

(2) INFORMATION FOR SEQ ID NO:13:

(i) SEQUENCE CHARACTERISTICS:
        (A) LENGTH:12 amino acids
        (B) TYPE:amino acid
        (D) TOPOLOGY:linear (ii) MOLECULE TYPE:peptide
        (A) DESCRIPTION: MAPKK peptide antigen; Table 5; CKKPTPIQLNPS (ix) SEQUENCE DESCRIPTION: SEQ ID NO:13:

Cys Lys Lys Pro Thr Pro Ile Gln Leu Asn Pro Ser
                5                          10

(2) INFORMATION FOR SEQ ID NO:14:

(i) SEQUENCE CHARACTERISTICS:
        (A) LENGTH:10 amino acids
        (B) TYPE:amino acid
        (D) TOPOLOGY:linear (ii) MOLECULE TYPE:peptide
        (A) DESCRIPTION: MAPKK peptide antigen; Table 5; CKLIHLEITQ (ix) SEQUENCE DESCRIPTION: SEQ ID NO:14:

Cys Lys Leu Ile His Leu Glu Ile Thr Gln
                5                    10

(2) INFORMATION FOR SEQ ID NO:15:

(i) SEQUENCE CHARACTERISTICS:
        (A) LENGTH:18 amino acids
        (B) TYPE:amino acid
        (D) TOPOLOGY:linear (ii) MOLECULE TYPE:peptide
        (A) DESCRIPTION: MAPKK peptide antigen;
            Table 5; CSTIGLAGPSTPTHAAGV (ix) SEQUENCE DESCRIPTION: SEQ ID NO:15:

Cys Ser Thr Ile Gly Leu Ala Gly Pro Ser Thr Pro Thr His Ala Ala Gly Val
                    5                        10                    15

(2) INFORMATION FOR SEQ ID NO:16:

(i) SEQUENCE CHARACTERISTICS:
        (A) LENGTH:16 amino acids
        (B) TYPE:amino acid
        (D) TOPOLOGY:linear (ii) MOLECULE TYPE:peptide
        (A) DESCRIPTION: MAPKK peptide antigen;
            Table 5; SVLGLIGEPIRGAKKC (ix) SEQUENCE DESCRIPTION: SEQ ID NO:16:

Ser Val Leu Gly Leu Ile Gly Glu Pro Ile Arg Gly Ala Lys Lys Cys
                  5                      10              15

(2) INFORMATION FOR SEQ ID NO:17:

(i) SEQUENCE CHARACTERISTICS:
        (A) LENGTH:19 amino acids
        (B) TYPE:amino acid
        (D) TOPOLOGY:linear (ii) MOLECULE TYPE:peptide
        (A) DESCRIPTION: TEY peptide;PEHDHTGFLTEYVATRWYR (ix) SEQUENCE DESCRIPTION: SEQ ID NO:17:

Pro Glu His Asp His Thr Gly Phe Leu Thr Glu Tyr Val Ala Thr Arg Trp Tyr
              5                       10                  15

(2) INFORMATION FOR SEQ ID NO:18:

(i) SEQUENCE CHARACTERISTICS:
        (A) LENGTH:20 amino acids
        (B) TYPE:amino acid
        (D) TOPOLOGY:linear (ii) MOLECULE TYPE:peptide
        (A) DESCRIPTION: PKI peptide; TTYADFIASGRTGRRNAIHD (ix) SEQUENCE DESCRIPTION: SEQ ID NO:18:

Thr Thr Tyr Ala Asp Phe Ile Ala Ser Gly Arg Thr Gly Arg Arg
              5                       10                  15

Asn Ala Ile His Asp
              20

(2) INFORMATION FOR SEQ ID NO:19 :

(i) SEQUENCE CHARACTERISTICS:
        (A) LENGTH:10 amino acids
        (B) TYPE:amino acid
        (D) TOPOLOGY:linear (ii) MOLECULE TYPE:peptide
        (A) DESCRIPTION:ETE peptide; RRREEETEEE (ix) SEQUENCE DESCRIPTION: SEQ ID NO:19:

Arg Arg Arg Glu Glu Glu Thr Glu Glu Glu
              5                       10

(2) INFORMATION FOR SEQ ID NO:20 :

(i) SEQUENCE CHARACTERISTICS:
        (A) LENGTH:13 amino acids
        (B) TYPE:amino acid
        (D) TOPOLOGY:linear (ii) MOLECULE TYPE:peptide
        (A) DESCRIPTION:RR-SRC peptide; RRLIEDAEYAARG (ix) SEQUENCE DESCRIPTION: SEQ ID NO:20:

Arg Arg Leu Ile Glu Asp Ala Glu Tyr Ala Ala Arg Gly
              5                       10

(2) INFORMATION FOR SEQ ID NO:21 :

(i) SEQUENCE CHARACTERISTICS:
        (A) LENGTH:15 amino acids
        (B) TYPE:amino acid
        (D) TOPOLOGY:linear (ii) MOLECULE TYPE:peptide
        (A) DESCRIPTION:Syntide-2; PLARTLSVAGLPGKK (ix) SEQUENCE DESCRIPTION: SEQ ID NO:21:

Pro Leu Ala Arg Thr Leu Ser Val Ala Gly Leu Pro Gly Lys Lys
              5                       10                  15

(2) INFORMATION FOR SEQ ID NO:22 :

(i) SEQUENCE CHARACTERISTICS:
        (A) LENGTH:8 amino acids
        (B) TYPE:amino acid
        (D) TOPOLOGY:linear (ii) MOLECULE TYPE:peptide
        (A) DESCRIPTION:S6 peptide; RRLSSLRA ( i x ) SEQUENCE DESCRIPTION: SEQ ID NO:22:

Arg Arg Leu Ser Ser Leu Arg Ala
                  5

( 2 ) INFORMATION FOR SEQ ID NO:23:

( i ) SEQUENCE CHARACTERISTICS:
         ( A ) LENGTH:16 amino acids
         ( B ) TYPE:amino acid
         ( D ) TOPOLOGY:linear ( i i ) MOLECULE TYPE:peptide
         ( A ) DESCRIPTION:Band-3 peptide; MEELQDDYEDDMEERR ( i x ) SEQUENCE DESCRIPTION: SEQ ID NO:23:

Met Glu Glu Leu Gln Asp Asp Tyr Glu Asp Asp Met Glu Glu Arg Arg
              5                   10                  15

( 2 ) INFORMATION FOR SEQ ID NO:24:

( i ) SEQUENCE CHARACTERISTICS:
         ( A ) LENGTH:12 amino acids
         ( B ) TYPE:amino acid
         ( D ) TOPOLOGY:linear ( i i ) MOLECULE TYPE:peptide
         ( A ) DESCRIPTION:Peptide CKKPTPIQLNPS; from 4-13 of MAPKK1a
               sequence ( i x ) SEQUENCE DESCRIPTION: SEQ ID NO:24:

Cys Lys Lys Pro Thr Pro Ile Gln Leu Asn Pro Ser
                  5                   10

( 2 ) INFORMATION FOR SEQ ID NO:25:

( i ) SEQUENCE CHARACTERISTICS:
         ( A ) LENGTH:36 base pairs
         ( B ) TYPE:nucleic acid
         ( C ) STRANDEDNESS:single
         ( D ) TOPOLOGY:linear ( i i ) MOLECULE TYPE:oligonucleotide
         ( A ) DESCRIPTION:modification of MAPKK1a cDNA for transfection ( i x ) SEQUENCE DESCRIPTION: SEQ ID NO:25:

GGATCCGCCG CCACCATGGC ACCCAAGAAG AAGCCG    36

( 2 ) INFORMATION FOR SEQ ID NO:26:

( i ) SEQUENCE CHARACTERISTICS:
         ( A ) LENGTH:23 amino acids
         ( B ) TYPE:amino acid
         ( C ) STRANDEDNESS:single
         ( D ) TOPOLOGY:linear ( i i ) MOLECULE TYPE:peptide
         ( A ) DESCRIPTION:56S sequence for construction of
               degenerate PCR primers; Table 4

( i x ) SEQUENCE DESCRIPTION: SEQ ID NO:26:

Ala Ala Arg Ala Thr His Gly Ala Arg Gly Ala Arg Tyr Thr Asn
                  5                   10                  15
Gly Gly Asn Gly Cys Asn Gly Ala
                  20

( 2 ) INFORMATION FOR SEQ ID NO:27:

( i ) SEQUENCE CHARACTERISTICS:

( A ) LENGTH:22 amino acids
( B ) TYPE:amino acid
( C ) STRANDEDNESS:single
( D ) TOPOLOGY:linear ( i i ) MOLECULE TYPE:peptide
( A ) DESCRIPTION:56A sequence for construction of degenerate PCR primers; Table 4

( i x ) SEQUENCE DESCRIPTION: SEQ ID NO:27:

Thr Cys Asn Gly Cys Asn Cys Cys Asn Arg Tyr Thr Cys Tyr Thr
                  5                   10                  15
Cys Asp Ala Thr Tyr Thr Thr
                20

( 2 ) INFORMATION FOR SEQ ID NO:28:

( i ) SEQUENCE CHARACTERISTICS:
( A ) LENGTH:23 amino acids
( B ) TYPE:amino acid
( C ) STRANDEDNESS:single
( D ) TOPOLOGY:linear ( i i ) MOLECULE TYPE: peptide
( A ) DESCRIPTION:59S sequence for construction of degenerate PCR primers; Table 4

( i x ) SEQUENCE DESCRIPTION: SEQ ID NO:28:

Ala Thr His Cys Ala Tyr Cys Thr Val Gly Ala Arg Ala Thr Met
                  5                   10                  15
Ala Cys Asp Cys Ala Val Ala Ala
                20

( 2 ) INFORMATION FOR SEQ ID NO:29:

( i ) SEQUENCE CHARACTERISTICS:
( A ) LENGTH:23 amino acids
( B ) TYPE:amino acid
( C ) STRANDEDNESS:single
( D ) TOPOLOGY:linear ( i i ) MOLECULE TYPE:peptide
( A ) DESCRIPTION:59A sequence for construction of degenerate PCR primers; Table 4

( i x ) SEQUENCE DESCRIPTION: SEQ ID NO:29:

Thr Thr Tyr Thr Gly Asn Gly Thr Asp Ala Thr Tyr Thr Cys Asn
                  5                   10                  15
Ala Gly Arg Thr Gly Asp Ala Thr
                20

( 2 ) INFORMATION FOR SEQ ID NO:30:

( i ) SEQUENCE CHARACTERISTICS:
( A ) LENGTH:23 amino acids
( B ) TYPE:amino acid
( C ) STRANDEDNESS:single
( D ) TOPOLOGY:linear ( i i ) MOLECULE TYPE:peptide
( A ) DESCRIPTION:57S sequence for construction of degenerate PCR primers; Table 4

( i x ) SEQUENCE DESCRIPTION: SEQ ID NO:30:

Cys Cys Asn Ala Cys Asn Cys Cys Asn Ala Thr His Cys Ala Arg
                  5                   10                  15
Tyr Thr Asn Ala Ala Tyr Cys Cys
                20

( 2 ) INFORMATION FOR SEQ ID NO:31:

( i ) SEQUENCE CHARACTERISTICS:
        ( A ) LENGTH:23 amino acids
        ( B ) TYPE:amino acid
        ( C ) STRANDEDNESS:single
        ( D ) TOPOLOGY:linear ( i i ) MOLECULE TYPE:peptide
        ( A ) DESCRIPTION:57A sequence for construction of
            degenerate PCR primers; Table 4

( i x ) SEQUENCE DESCRIPTION: SEQ ID NO:31:

```
Gly Gly Arg Thr Thr Asn Ala Arg Tyr Thr Gly Asp Ala Thr Asn
              5                   10                  15
Gly Gly Asn Gly Thr Asn Gly Gly
              20
```

( 2 ) INFORMATION FOR SEQ ID NO:32:

( i ) SEQUENCE CHARACTERISTICS:
        ( A ) LENGTH:1455 base pairs
        ( B ) TYPE:nucleic acid
        ( C ) STRANDEDNESS:single
        ( D ) TOPOLOGY:linear ( i i ) MOLECULE TYPE: cDNA
        ( A ) DESCRIPTION:MAPKK1a cDNA; FIGURE 10

( i x ) SEQUENCE DESCRIPTION: SEQ ID NO:32:

```
GGCGGAGTTG GAAGCGCGTT ACCCGGGTCC AAAATGCCCA AGAAGAAGCC GACGCCCATC   60
CAGCTGAACC CGGCCCCCGA CGGCTCTGCA GTTAACGGGA CCAGCTCTGC GGAGACCAAC  120
TTGGAGGCCT TGCAGAAGAA GCTGGAGGAG CTAGAGCTTG ATGAGCAGCA GCGAAAGCGC  180
CTTGAGGCCT TTCTTACCCA GAAGCAGAAG GTGGGAGAAC TGAAGGATGA CGACTTTGAG  240
AAGATCAGTG AGCTGGGGGC TGGCAATGGC GGTGTGGTGT TCAAGGTCTC CCACAAGCCT  300
TCTGGCCTGG TCATGGCCAG AAAGCTAATT CATCTGGAGA TCAAACCCGC AATCCGGAAC  360
CAGATCATAA GGGAGCTGCA GGTTCTGCAT GAGTGCAACT CTCCGTACAT CGTGGGCTTC  420
TATGGTGCGT TCTACAGCGA TGGCGAGATC AGTATCTGCA TGGAGCACAT GGATGGAGGT  480
TCTCTGGATC AAGTCCTGAA GAAAGCTGGA AGAATTCCTG AACAAATTTT AGGAAAAGTT  540
AGCATTGCTG TAATAAAAGG CCTGACATAT CTGAGGGAGA AGCACAAGAT CATGCACAGA  600
GATGTCAAGC CCTCCAACAT CCTAGTCAAC TCCCGTGGGG AGATCAAGCT CTGTGACTTT  660
GGGGTCAGCG GCAGCTCAT CGACTCCATG GCCAACTCCT TCGTGGGCAC AAGGTCCTAC  720
ATGTCGCCAG AAAGACTCCA GGGGACTCAT TACTCTGTGC AGTCAGACAT CTGGAGCATG  780
GGACTGTCTC TGGTAGAGAT GGCGGTTGGG AGGTATCCCA TCCCTCCTCC AGATGCCAAG  840
GAGCTGGAGC TGATGTTTGG GTGCCAGGTG GAAGGAGATG CGGCTGAGAC CCCACCCAGG  900
CCAAGGACCC CCGGGAGGCC CCTTAGCTCA TACGGAATGG ACAGCCGACC TCCCATGGCA  960
ATTTTTGAGT TGTTGGATTA CATAGTCAAC GAGCCTCCTC CAAAACTGCC CAGTGGAGTG 1020
TTCAGTCTGG AATTTCAAGA TTTTGTGAAT AAATGCTTAA TAAAAAACCC GCAGAGAGA 1080
GCAGATTTGA AGCAACTCAT GGTTCATGCT TTTATCAAGA GATCTGATGC TGAGGAAGTG 1140
GATTTTGCAG GTTGGCTCTG CTCCACCATC GGCCTTAACC AGCCCAGCAC ACCAACCCAT 1200
GCTGCTGGCG TCTAAGTGTT TGGGAAGCAA CAAAGAGCGA GTCCCTGCC CGGTGGTTTG 1260
CCATGTCGCT TTTGGGCCTC CTTCCCATGC CTGTCTCTGT TCAGATGTGC ATTTCACCTG 1320
TGACAAAGGA TGAAGAACAC AGCATGTGCC AAGATTCTAC TCTTGTCATT TTTAATATTA 1380
```

CTGTCTTTAT TCTTATTACT ATTATTGTTC CCCTAAGTGG ATTGGCTTTG TGCTTGGGGC 1440

TATTTGTGTG TATCC 1455

( 2 ) INFORMATION FOR SEQ ID NO:33:

( i ) SEQUENCE CHARACTERISTICS:
        ( A ) LENGTH:393 amino acids
        ( B ) TYPE:amino acid
        ( D ) TOPOLOGY:linear ( i i ) MOLECULE TYPE: polypeptide
        ( A ) DESCRIPTION:MAPKK1a protein; FIGURE 10

( i x ) SEQUENCE DESCRIPTION: SEQ ID NO:33:

```
Met Pro Lys Lys Lys Pro Thr Pro Ile Gln Leu Asn Pro Ala Pro
              5                   10                  15

Asp Gly Ser Ala Val Asn Gly Thr Ser Ser Ala Glu Thr Asn Leu
              20                  25                  30

Glu Ala Leu Gln Lys Lys Leu Glu Glu Leu Glu Leu Asp Glu Gln
              35                  40                  45

Gln Arg Lys Arg Leu Glu Ala Phe Leu Thr Gln Lys Gln Lys Val
              50                  55                  60

Gly Glu Leu Lys Asp Asp Phe Glu Lys Ile Ser Glu Leu Gly
              65                  70                  75

Ala Gly Asn Gly Gly Val Val Phe Lys Val Ser His Lys Pro Ser
              80                  85                  90

Gly Leu Val Met Ala Arg Lys Leu Ile His Leu Glu Ile Lys Pro
              95                  100                 105

Ala Ile Arg Asn Gln Ile Ile Arg Glu Leu Gln Val Leu His Glu
              110                 115                 120

Cys Asn Ser Pro Tyr Ile Val Gly Phe Tyr Gly Ala Phe Tyr Ser
              125                 130                 135

Asp Gly Glu Ile Ser Ile Cys Met Glu His Met Asp Gly Gly Ser
              140                 145                 150

Leu Asp Gln Val Leu Lys Lys Ala Gly Arg Ile Pro Glu Gln Ile
              155                 160                 165

Leu Gly Lys Val Ser Ile Ala Val Ile Lys Gly Leu Thr Tyr Leu
              170                 175                 180

Arg Glu Lys His Lys Ile Met His Arg Asp Val Lys Pro Ser Asn
              185                 190                 195

Ile Leu Val Asn Ser Arg Gly Glu Ile Lys Leu Cys Asp Phe Gly
              200                 205                 210

Val Ser Gly Gln Leu Ile Asp Ser Met Ala Asn Ser Phe Val Gly
              215                 220                 225

Thr Arg Ser Tyr Met Ser Pro Glu Arg Leu Gln Gly Thr His Tyr
              230                 235                 240

Ser Val Gln Ser Asp Ile Trp Ser Met Gly Leu Ser Leu Val Glu
              245                 250                 255

Met Ala Val Gly Arg Tyr Pro Ile Pro Pro Asp Ala Lys Glu
              260                 265                 270

Leu Glu Leu Met Phe Gly Cys Gln Val Glu Gly Asp Ala Ala Glu
              275                 280                 285

Thr Pro Pro Arg Pro Arg Thr Pro Gly Arg Pro Leu Ser Ser Tyr
              290                 295                 300

Gly Met Asp Ser Arg Pro Pro Met Ala Ile Phe Glu Leu Leu Asp
              305                 310                 315
```

| Tyr | Ile | Val | Asn | Glu | Pro | Pro | Pro | Lys | Leu | Pro | Ser | Gly | Val | Phe |
|---|---|---|---|---|---|---|---|---|---|---|---|---|---|---|
| | | | | 320 | | | | 325 | | | | | | 330 |

| Ser | Leu | Glu | Phe | Gln | Asp | Phe | Val | Asn | Lys | Cys | Leu | Ile | Lys | Asn |
|---|---|---|---|---|---|---|---|---|---|---|---|---|---|---|
| | | | | 335 | | | | 340 | | | | | | 345 |

| Pro | Ala | Glu | Arg | Ala | Asp | Leu | Lys | Gln | Leu | Met | Val | His | Ala | Phe |
|---|---|---|---|---|---|---|---|---|---|---|---|---|---|---|
| | | | | 350 | | | | 355 | | | | | | 360 |

| Ile | Lys | Arg | Ser | Asp | Ala | Glu | Glu | Val | Asp | Phe | Ala | Gly | Trp | Leu |
|---|---|---|---|---|---|---|---|---|---|---|---|---|---|---|
| | | | | 365 | | | | 370 | | | | | | 375 |

| Cys | Ser | Thr | Ile | Gly | Leu | Asn | Gln | Pro | Ser | Thr | Pro | Thr | His | Ala |
|---|---|---|---|---|---|---|---|---|---|---|---|---|---|---|
| | | | | 380 | | | | 385 | | | | | | 390 |

| Ala | Gly | Val |
|---|---|---|
| | | 393 |

( 2 ) INFORMATION FOR SEQ ID NO:34:

( i ) SEQUENCE CHARACTERISTICS:
        ( A ) LENGTH:1162 base pairs
        ( B ) TYPE:nucleic acid
        ( C ) STRANDEDNESS:single
        ( D ) TOPOLOGY:linear ( i i ) MOLECULE TYPE: cDNA
        ( A ) DESCRIPTION:MAPKK1b cDNA; FIGURE 14A ( i x ) SEQUENCE DESCRIPTION: SEQ ID NO:34:

```
GAGTTGGAAG CGCGTTACCC GGGTCCAAAA TGCCCAAGAA GAAGCCGACG CCCATCCAGC   60
TGAACCCGGC CCCCGACGGC TCTGCAGTTA ACGGGACCAG CTCTGCGGAG ACCAACTTGG  120
AGGCCTTGCA GAAGAAGCTG GAGGAGCTAG AGCTTGATGA GCAGCAGCGA AAGCGCCTTG  180
AGGCCTTTCT TACCCAGAAG CAGAAGGTGG GAGAACTGAA GGATGACGAC TTTGAGAAGA  240
TCAGTGAGCT GGGGGCTGGC AATGGCGGTG TGGTGTTCAA GGTCTCCCAC AAGCCTTCTG  300
GCCTGGTCAT GGCCAGAAAG CTAATTCATC TGGAGATCAA ACCCGCAATC CGGAACCAGA  360
TCATAAGGGA GCTGCAGGTT CTGCATGAGT GCAACTCTCC GTACATCGTG GGCTTCTATG  420
GTGCGTTCTA CAGCGATGGC GAGATCAGTA TCTGCATGGA GCACATGGTA ATAAAAGGCC  480
TGACATATCT GAGGGAGAAG CACAAGATCA TGCACAGAGA TGTCAAGCCC TCCAACATCC  540
TAGTCAACTC CCGTGGGGAG ATCAAGCTCT GTGACTTTGG GGTCAGCGGG CAGCTCATCG  600
ACTCCATGGC CAACTCCTTC GTGGGCACAA GGTCCTACAT GTCGCCAGAA AGACTCCAGG  660
GGACTCATTA CTCTGTGCAG TCAGACATCT GGAGCATGGG ACTGTCTCTG GTAGAGATGG  720
CGGTTGGGAG GTATCCCATC CCTCCTCCAG ATGCCAAGGA GCTGGAGCTG ATGTTTGGGT  780
GCCAGGTGGA AGGAGATGCG GCTGAGACCC CACCCAGGCC AAGGACCCCC GGGAGGCCCC  840
TTAGCTCATA CGGAATGGAC AGCCGACCTC CCATGGCAAT TTTTGAGTTG TTGGATTACA  900
TAGTCAACGA GCCTCCTCCA AAACTGCCCA GTGGAGTGTT CAGTCTGGAA TTTCAAGATT  960
TTGTGAATAA ATGCTTAATA AAAAACCCCG CAGAGAGAGC AGATTTGAAG CAACTCATGG 1020
TTCATGCTTT TATCAAGAGA TCTGATGCTG AGGAAGTGGA TTTTGCAGGT TGGCTCTGCT 1080
CCACCATCGG CCTTAACCAG CCCAGCACAC CAACCCATGC TGCTGGCGTC TAAGTGTTTG 1140
GGAAGCAACA AAGAGCGAGT CC                                         1162
```

( 2 ) INFORMATION FOR SEQ ID NO:35:

( i ) SEQUENCE CHARACTERISTICS:
        ( A ) LENGTH:368 amino acids
        ( B ) TYPE:amino acid
        ( D ) TOPOLOGY:linear ( i i ) MOLECULE TYPE: polypeptide
  ( A ) DESCRIPTION:MAPKK1b protein; FIGURE 14B ( i x ) SEQUENCE DESCRIPTION: SEQ ID NO:35:

```
Met Pro Lys Lys Lys Pro Thr Pro Ile Gln Leu Asn Pro Ala Pro
              5                  10                  15
Asp Gly Ser Ala Val Asn Gly Thr Ser Ser Ala Glu Thr Asn Leu
             20                  25                  30
Glu Ala Leu Gln Lys Lys Leu Glu Glu Leu Glu Leu Asp Glu Gln
             35                  40                  45
Gln Arg Lys Arg Leu Glu Ala Phe Leu Thr Gln Lys Gln Lys Val
             50                  55                  60
Gly Glu Leu Lys Asp Asp Phe Glu Lys Ile Ser Glu Leu Gly
             65                  70                  75
Ala Gly Asn Gly Gly Val Val Phe Lys Val Ser His Lys Pro Ser
             80                  85                  90
Gly Leu Val Met Ala Arg Lys Leu Ile His Leu Glu Ile Lys Pro
             95                 100                 105
Ala Ile Arg Asn Gln Ile Ile Arg Glu Leu Gln Val Leu His Glu
            110                 115                 120
Cys Asn Ser Pro Tyr Ile Val Gly Phe Tyr Gly Ala Phe Tyr Ser
            125                 130                 135
Asp Gly Glu Ile Ser Ile Cys Met Glu His Met Val Ile Lys Gly
            140                 145                 150
Leu Thr Tyr Leu Arg Glu Lys His Lys Ile Met His Arg Asp Val
            155                 160                 165
Lys Pro Ser Asn Ile Leu Val Asn Ser Arg Gly Glu Ile Lys Leu
            170                 175                 180
Cys Asp Phe Gly Val Ser Gly Gln Leu Ile Asp Ser Met Ala Asn
            185                 190                 195
Ser Phe Val Gly Thr Arg Ser Tyr Met Ser Pro Glu Arg Leu Gln
            200                 205                 210
Gly Thr His Tyr Ser Val Gln Ser Asp Ile Trp Ser Met Gly Leu
            215                 220                 225
Ser Leu Val Glu Met Ala Val Gly Arg Tyr Pro Ile Pro Pro Pro
            230                 235                 240
Asp Ala Lys Glu Leu Glu Leu Met Phe Gly Cys Gln Val Glu Gly
            245                 250                 255
Asp Ala Ala Glu Thr Pro Pro Arg Pro Arg Thr Pro Gly Arg
            260                 265                 270
Pro Leu Ser Ser Tyr Gly Met Asp Ser Arg Pro Pro Met Ala Ile
            275                 280                 285
Phe Gln Leu Leu Asp Tyr Ile Val Asn Glu Pro Pro Pro Lys Leu
            290                 295                 300
Pro Ser Gly Val Phe Ser Leu Glu Phe Gln Asp Phe Val Asn Lys
            305                 310                 315
Cys Leu Ile Lys Asn Pro Ala Glu Arg Ala Asp Leu Lys Gln Leu
            320                 325                 330
Met Val His Ala Phe Ile Lys Arg Ser Asp Ala Glu Glu Val Asp
            335                 340                 345
Phe Ala Gly Trp Leu Cys Ser Thr Ile Gly Leu Asn Gln Pro Ser
            350                 355                 360
Thr Pro Thr His Ala Ala Gly Val
            365
```

( 2 ) INFORMATION FOR SEQ ID NO:36:

( i ) SEQUENCE CHARACTERISTICS:
        ( A ) LENGTH:1104 base pairs
        ( B ) TYPE:nucleic acid
        ( C ) STRANDEDNESS:single
        ( D ) TOPOLOGY:linear ( i i ) MOLECULE TYPE: cDNA
        ( A ) DESCRIPTION:MAPKK1b coding sequence; FIGURE 10, bases
        34-471 and 550-1212

( i x ) SEQUENCE DESCRIPTION: SEQ ID NO:36:

```
ATGCCCAAGA AGAAGCCGAC GCCCATCCAG CTGAACCCGG CCCCCGACGG CTCTGCAGTT    60
AACGGGACCA GCTCTGCGGA GACCAACTTG GAGGCCTTGC AGAAGAAGCT GGAGGAGCTA   120
GAGCTTGATG AGCAGCAGCG AAAGCGCCTT GAGGCCTTTC TTACCCAGAA GCAGAAGGTG   180
GGAGAACTGA AGGATGACGA CTTTGAGAAG ATCAGTGAGC TGGGGGCGGT GTGGTGTTGG   240
CAATGGCTCA AGGTCTCCCA CAAGCCTTCT GGCCTGGTCA TGGCCAGAAA GCTAATTCAT   300
CTGGAGATCA AACCCGCAAT CCGGAACCAG ATCATAAGGG AGCTGCAGGT TCTGCATGAG   360
TGCAACTCTC CGTACATCGT GGGCTTCTAT GGTGCGTTCT ACAGCGATGG CGAGATCAGT   420
ATCTGCATGG AGCACATGGT AATAAAAGGC CTGACATATC TGAGGGAGAA GCACAAGATC   480
ATGCACAGAG ATGTCAAGCC CTCCAACATC CTAGTCAACT CCCGTGGGGA GATCAAGCTC   540
TGTGACTTTG GGGTCAGCGG GCAGCTCATC GACTCCATGG CCAACTCCTT CGTGGGCACA   600
AGGTCCTACA TGTCGCCAGA AAGACTCCAG GGGACTCATT ACTCTGTGCA GTCAGACATC   660
TGGAGCATGG GACTGTCTCT GGTAGAGATG GCGGTTGGGA GGTATCCCAT CCCTCCTCCA   720
GATGCCAAGG AGCTGGAGCT GATGTTTGGG TGCCAGGTGG AAGGAGATGC GGCTGAGACC   780
CCACCCAGGC CAAGGACCCC CGGGAGGCCC CTTAGCTCAT ACGGAATGGA CAGCCGACCT   840
CCCATGGCAA TTTTTGAGTT GTTGGATTAC ATAGTCAACG AGCCTCCTCC AAAACTGCCC   900
AGTGGAGTGT TCAGTCTGGA ATTTCAAGAT TTTGTGAATA AATGCTTAAT AAAAAACCCC   960
GCAGAGAGAG CAGATTTGAA GCAACTCATG GTTCATGCTT TTATCAAGAG ATCTGATGCT  1020
GAGGAAGTGG ATTTTGCAGG TTGGCTCTGC TCCACCATCG GCCTTAACCA GCCCAGCACA  1080
CCAACCCATG CTGCTGGCGT CTAA                                         1104
```